US007883707B2

(12) United States Patent
Kakkis et al.

(10) Patent No.: US 7,883,707 B2
(45) Date of Patent: *Feb. 8, 2011

(54) INDUCTION OF ANTIGEN SPECIFIC IMMUNNOLOGIC TOLERANCE

(76) Inventors: Emil D. Kakkis, 2512 Laguna Vista Dr., Novato, CA (US) 94949; Thomas Lester, 23632 Kentworthy Ave., Harbor City, CA (US) 90710; Merry Passage, 19723 Ronald Ave., Torrance, CA (US) 95053; Christopher Tanaka, 15818 Denker Ave., Apt. E, Gardena, CA (US) 90247; Rebecca Yang, 4225 Via Arbolada #559, Los Angeles, CA (US) 90042

( * ) Notice: Subject to any disclaimer, the term of this patent is extended or adjusted under 35 U.S.C. 154(b) by 0 days.

This patent is subject to a terminal disclaimer.

(21) Appl. No.: 12/412,986

(22) Filed: Mar. 27, 2009

(65) Prior Publication Data

US 2009/0238818 A1 Sep. 24, 2009

Related U.S. Application Data

(63) Continuation of application No. 10/429,314, filed on May 5, 2003, now abandoned, which is a continuation-in-part of application No. 10/141,668, filed on May 6, 2002, now Pat. No. 7,485,314.

(51) Int. Cl.
*A61K 39/385* (2006.01)
(52) U.S. Cl. .................................. 424/193.1; 424/198.1
(58) Field of Classification Search ........................ None
See application file for complete search history.

(56) References Cited

U.S. PATENT DOCUMENTS

| 4,117,118 | A | 9/1978 | Harri et al. |
| 5,135,915 | A | 8/1992 | Czarniecki et al. |
| 5,597,563 | A | 1/1997 | Beschorner |
| 5,747,034 | A | 5/1998 | de Boer et al. |
| 5,837,812 | A | 11/1998 | Harrison et al. |
| 6,149,909 | A | 11/2000 | Scott et al. |

FOREIGN PATENT DOCUMENTS

| WO | WO-90/03812 | 4/1990 |
| WO | WO-93/15750 | 8/1993 |
| WO | WO-96/23882 | 8/1996 |
| WO | WO-98/37917 | 9/1998 |

OTHER PUBLICATIONS

Adams et al., Conventional immunosuppression and co-stimulation blockade. The Royal Society, doi 10.1098/rstb.2001.0854, pp. 703-705 (2001).
Aledort, Inhibitors in hemophilia patients: current status and management. *Am. J. Hematol.* 47: 208-17 (1994).
Amalfitano, Recombinant human acid alpha-glucosidase enzyme therapy for infantile glycogen storage disease type II: results of a phase I/II clinical trial. *Genet. Med.* 3:132-8 (2001).
Auchincloss H. Chapter 11, Transplantation Immunology, Bach and Auchincloss Eds., Wiley-Liss, New York, 211-8 (1995).
Bemer et al., Interleukin-2 down-modulates memory T helper lymphocyte development during antigenic stimulation in vitro. *Eur. J. Immunol.* 25: 3394-401 (1995).
Brady et al., Management of neutralizing antibody to ceredase in a patient with type 3 gaucher disearse, *Pediatrics.* 100: E11 (1997).
Brooks, Immuno response to enzyme replacement therapy in lysosomal storage disorder patients and animal models. *Molec. Genet. Metab.* 68: 172-9 (1999).
Cantor et al., Lysosomal enzyme phosphorylation. II. Protein recognition determinants in either lobe of procathepsin D are sufficient for phosphorylation of both the amino and carboxyl lobe oligosaccharides. *J. Biol. Chem.* 267: 23349-56 (1992).
Chaffee et al., IgG antibody response to polyethylene glycol-modified adenosine deaminase in patients with adenosine deaminase deficiency. *J. Clin. Invest.* 89:1643-51 (1993).
Chao et al., Induction of tolerance to human factor VIII in mice. *Blood.* 97: 3311-2 (2001).
Corsini et al., Long-term immunological changes in azathioprine-treated MS patients. *Neurol. Sci.* 21: 87-91 (2000).

(Continued)

*Primary Examiner*—Zachary Skelding
(74) *Attorney, Agent, or Firm*—Marshall, Gerstein & Borun LLP

(57) ABSTRACT

Antigen specific immune tolerance is induced in a mammalian host by administration of a toleragen in combination with a regimen of immunosuppression. The methods optionally include a preceding conditioning period, where immunosuppressive agents are administered in the absence of the toleragen. After the tolerizing regimen, the host is withdrawn from the suppressive agents, but is able to maintain specific immune tolerance to the immunogenic epitopes present on the toleragen. Optimally, the toleragen will have high uptake properties that allow uptake in vivo at low concentrations in a wide variety of tolerizing cell types.

37 Claims, 10 Drawing Sheets

OTHER PUBLICATIONS

Goodnow et al., Pathways for self-tolerance and the treatment of autoimmune diseases. *Lancet*. 357: 2115-21 (2001).

Gossain et al., Systemic allergy to human (recombinant DNA) insulin. *Ann. Allergy*. 55: 116-8 (1985).

Hohlfeld et al., Autoimmune concepts of multiple sclerosis as a basis for selective immunotherapy: From pipe dreams to (therapeutic) pipelines. *Proc. Natl. Acad. Sci. USA*. 101: 14599-606 (2004).

Huang et al., Retrovirus-mediated transfer of the human alpha-L-iduronidase cDNA into human hematopoietic progenitor cells leads to correction in trans of Hurler fibroblasts. *Gene Ther*. 4.; 115.0-9 (1997).

Janeway et al., Immunobiology, 5$^{th}$ Edition, Garland Science, 289, 556-9 (2001).

Kakavanos et al., Immuno tolerance after long-term enzyme-replacement therapy among patients who have mucopolysaccharidosis I, *Lancet*. 361: 1608-13 (2003).

Kakkis et al., Long-term and high-dose trials of enzyme replacement therapy in the canine model of mucopolysaccharidosis I. *Biochem. Mol. Med*. 58: 156-67 (1996).

Kakkis et al., Pravastatin increases survival and inhibits natural killer cell enhancement factor in liver transplanted rats. *J. Surg. Res*. 69: 393-8 (1997).

Kakkis et al., Enzyme-replacement therapy in mucopolysaccharidosis I. *N. Engl. J. Med*. 344: 182-8 (2001).

Kakkis et al., Overexpression of the human lysosomal enzyme alpha-L-iduronidase in Chinese hamster ovary cells. *Protein Expr. Purif*. 5: 225-32 (1994).

Kirk et al., Immunosuppression without immunosuppression? *Basic Science*. 1: 65-75 (1999).

Krensky et al., Immunologic tolerance. *Pediatr. Nephrol* 16:675-9 (2001).

Lechler et al., T-Cell anergy and peripheral T-cell tolerance. *The Royal Society*. 356: 625-37 (2001).

Lutzko et al., Genetically corrected autologous stem cells engraft, but host immune responses limit their utility in canine alpha-L-iduronidase deficiency. *Blood*. 93: 1895-905 (1999).

Marketletter, Autoimmune Shares Collapse on Colloral Data in Rheumatoid Arthritis, Markletter Publications Ltd., Sep. 13, 1999.

McHeyzer-Williams et al., B cell memory and the long-lived plasma cell. *Curr. Opin Immunol*. 11: 172-9 (1999).

Ponce et al., Enzyme therapy in gaucher disease type 1: Effect of neutralizing antibodies to acid beta-glucosidase. *Blood*. 90: 43-8 (1997).

Pozzilli et al., No effect of oral insulin on residual beta-cell function in recent-onset type I diabetes (the IMDIAB VII). IMDIAB Group. *Diabetologia*. 43:1000-4 (2000).

Richards et al., Antibody response in patients with gaucher disease after repeated infusion with macrophage-targeted glucocerebrosidase. Blood. 82:1402-1409 (1993).

Rosenberg et al., Immunosurveillance of alglucerase enzyme therapy for Gaucher patients: induction of humoral tolerance in seroconverted patients after repeat administration. *Blood*. 93: 2081-8 (1999).

Rossi et al., Long-term induction of immuno tolerance after blockage of CD40-CD40L interaction in a mouse model of hemophilia A. *Blood*. 97: 2750-7 (2001).

Schroeder et al., Tolerance and the "Holy Grail" of transplantation. *J. Surg. Res*. 111: 109-19 (2003).

Sebille et al., Mechanisms of tolerance induction: Blockade of co-stimulation. *The Royal Society*. 356: 649-57 (2001).

Shimizu et al., Stimulation of CD25+CD4+ regulatory T cells through GITR breaks immunological self-tolerance. *Nature Immunol*. 3: 135-142 (2002).

Shull et al., High frequency of acute promyelocytic leukemia among Latinos with acute myeloid leukemia. *Blood*. 88: 377-9 (1996).

Shull et al., Enzyme replacement in a canine model of Hurler Syndrome. *Nat. Acad. Sci. USA*. 91: 12937-41 (1994).

Shull et al., Enzyme replacement in a canine model of Hurler syndrome. Proc. Natl. Acad. Sci. USA. 91 :12937-41 (1994).

Stockinger et al., T lymphocyte tolerance: From thymic deletion to peripheral contol mechanism. *Adv. Immunol*. 71: 229-65 (1999).

Tisch et al., Antigen-specific immunotherapy: Is it a real possibility to combat T-cell-mediated autoimmunity? *Proc. Natl. Acad. Sci. USA*. 91: 437-8 (1994).

Tough et al., Fundamental Immunology, 5th Ed. (2003), ed. William E. Paul, Lippincott Williams and Wilkins, p. 865.

Weimer et al., Switch from cyclosporine A to tacrolimus in renal transplant recipients: impact on Th1, Th2, and monokine responses. *Hum. Immunol*. 61: 884-97 (2000).

Wilson et al., Immunomodulation to enhance gene therapy. *Nature Med*. 1: 887-9 (1995).

International Preliminary Report on Patentability, PCT/US2003/13843, dated Mar. 13, 2006.

International Search Report, PCT/US2003/13843, dated Dec. 11, 2003.

Dickson et al., Immune tolerance improves the efficacy of enzyme replacement therapy in canine mucopolysaccharidosis I. *J. Clin. Invest*. 118(8): 2868-76 (2008).

Jones et al., Multivalent thioether-peptide conjugates: B cell tolerance of an anti-peptide immune response. *Bioconjugate Chem*. 10(3): 480-8 (1999).

Kakkis, Enzyme replacement therapy for the mucopolysaccharide storage disorders. *Exp. Opin. Invest. Drugs*. 11(5): 675-85 (2002).

Kakkis et al., Successful induction of immune tolerance to enzyme replacement therapy in canine mucopolysaccharidosis I. *Proc. Natl. Acad. Sci. USA*. 101(3): 829-34 (2004).

Leung et al., Long-term complete remission and immune tolerance after intensive chemotherapy for lymphoproliferative disorders complicating live transplant. *Transplantation*. 67(11): 1487-9 (1999).

Lien et al., Complete remission and possible immune tolerance after multidrug combination chemotherapy for cyclosporine-related lymphoma in a renal transplant recipient with acute pancreatitis. *Transplantation*. 52(4): 739-42 (1991).

Ponder et al., Immune response hinders therapy for lysosomal storage diseases. *J. Clin. Invest*. 118(8): 2686-89 (2008).

Supplementary European Search Report, EP 03 72 6601, dated May 28, 2009.

INDUCTION OF ANTIGEN SPECIFIC IMMUNNOLOGIC TOLERANCE

The present application is a continuation of U.S. patent application Ser. No. 10/429,314, filed May 5, 2003, which is a continuation-in-part application of U.S. patent application Ser. No. 10/141,668, filed May 6, 2002. The entire text of the aforementioned applications are incorporated herein by reference.

FIELD OF THE INVENTION

The present application is directed to methods and compositions for inducing immune tolerance in a mammal. The methods comprise administration of a high-uptake toleragen in combination with immunosuppressive agents in a tolerization regimen.

BACKGROUND OF THE INVENTION

Immune tolerance is highly relevant to a wide range of clinically important applications. Antigen-specific tolerance induction is a major goal for the treatment or prevention of autoimmune disease and graft rejection, which are currently controlled by nonspecific, immunosuppressive therapies that result in increased rates of infections, cancers and drug-related pathology. Other applications of immune tolerance induction include allergies and asthma, bone marrow replacement and protein based therapeutics.

One of the first practical applications of molecular biology has been the ability to produce large quantities of rare biological agents, many of which have therapeutic activity. It has been found, however, that during administration of these agents, a patient can mount an immune response, leading to the production of antibodies that bind and interfere with the therapeutic activity as well as cause acute or chronic immunologic reactions. This problem is most significant for therapeutics that are proteins because proteins are complex antigens and in many cases, the patient is immunologically naïve to the antigens.

This type of immune response has been found in at least some patients with deficiency disorders such as hemophilia A (Aledort (1994) Am. J. Hemat. 47:208-217), diabetes mellitus (Gossain et al. (1985) Ann. Allergy 55:116-118), adenosine deaminase deficiency (Chaffee et al. (1993) J. Clin. Inv. 89:1643-1651), Gaucher disease (Richards et al. (1993) Blood 82:1402-1409), and Pompe disease (Amalfitano (2001) Genet Med 3:132-138. In hemophilia A, antibodies can inhibit factor VIII function requiring alternative treatment with activated prothrombin complex concentrates. In adenosine deaminase deficiency, antibodies to PEG modified adenosine deaminase enhance the clearance of the enzyme and lower its efficacy. In Gaucher disease, the induction of IgG1 antibodies has been associated with anaphylactoid reactions due to complement activation during infusions. In Pompe disease, replacement therapy with recombinant alpha-glucosidase resulted in the induction of antibodies in two of three patients treated, which resulted in declining efficacy of the therapy.

Similar immune responses have been found in the delivery of protein therapeutics by gene therapy. For example, viral proteins associated with vectors are targets of an immune response that can cause inflammation, shortened expression and prevented repeat administration of vector (Wilson and Kay (1995) Nature Med. 1:887-889). Antibody responses to the therapeutic protein have also been observed in gene therapy experiments and are part of an overall immune response that prevents long-term expression (Shull et al. (1996) Blood 88:377-379). Generalized immune suppression, blockade and immune deviation from humoral to cellular responses have been utilized to address this problem, but are not likely to ensure long lasting tolerance to the antigen.

Tolerance may be defined as the absence of an immune response to a specific antigen in the setting of an otherwise normal immune system. This state of specific immunological tolerance to self-components involves both central and peripheral mechanisms. Central tolerance (negative selection) is a consequence of immature T cells receiving strong intracellular signaling while still resident in the thymus, resulting in clonal deletion of autoreactive cells. Peripheral tolerance occurs when the immune system becomes unreactive to an antigen presented in the periphery, where, in contrast to the thymus, T cells are assumed to be functionally mature. Peripheral tolerance has been proposed to be the result of various mechanisms, including the development of antigen specific suppressor cells or other means of active tolerance, clonal deletion, and anergy. Autoreactive cells may be physically deleted by the induction of apoptosis after recognition of tolerizing antigen, may become anergic without deletion, or may be functionally inhibited by regulatory cytokines or cells. Although much has been learned in recent years, it is still difficult to predict the outcome of antigenic exposure in vivo, and further elucidation of tolerance mechanisms is needed at the basic level.

Numerous strategies have been developed to induce antigen specific tolerance in animal models, for example with respect to autoimmune disorders, such as multiple sclerosis (or experimental allergic encephalitis, EAE) or diabetes, as well as to prevent rejection of allogeneic tissue transplants. The major methods developed in mouse and rat models involve administration of high doses of soluble antigen, oral ingestion of antigens or intrathymic injection. The efficacy of these methods depends to varying degrees on clonal deletion, clonal anergy, active suppression by antigen-specific T cells and immune deviation from cellular to humoral immune responses.

Although administration of large quantities of soluble antigens has long been known to induce non-responsiveness to subsequent immunological challenge, studies of EAE have also highlighted the difficulties in this approach. The high doses required and the inconsistency of tolerance versus immune deviation make soluble antigen administration alone impractical for most gene therapy situations.

Administration of very large doses of antigen orally to mice has also been demonstrated to induce tolerance to protein antigens. However, extraordinary doses are required, and the results are complex. Certain doses are found to result in anergy, while other doses induce a form of antigen-specific bystander suppression, characterized by antigen-specific TH2 type responses. In addition, oral antigen can sensitize the immune system and lead to more severe disease.

Intrathymic injection of antigens or cells has been widely explored as a technique to induce central immune tolerance. Antigens injected and presented within the thymus can cause apoptosis or anergy of $CD4^+$, $CD8^+$ T cells in a process that may take up to 10 days. Like oral and soluble antigen tolerance, the tolerizing effect is dose dependent: low doses of antigen are sensitizing or provide only partial protection, whereas larger doses of antigen are tolerizing. The context of antigen presentation within the thymus is also important. Tolerance is most efficiently induced when the antigens are presented by host antigen presenting cells (APC). Once tolerized, the continued presence of antigen within the animal is needed for maintenance of tolerance, and depletion of mature T cells may also be required.

One strategy for tolerance induction is based on the discovery that optimal T cell activation requires both antigen-specific signals and non-antigen-specific signals. During antigen presentation, a variety of important bidirectional cognate interactions take place, with signaling to both the T cell and the antigen presenting cell. The best understood costimulatory signal is provided through the T cell surface molecule CD28. CD28 has two ligands, the homologous molecules CD80 (B7-1) and CD86 (B7-2); both are expressed on activated APC and some other cell types. Another pathway that has received significant attention and is important in T cell costimulation is that mediated by CD40 and its ligand CD154. CD154 is expressed on activated T cells, primarily $CD4^+$ T cells.

In the past several years, a variety of laboratories have shown that blockade of T cell costimulatory signals can improve long-term allograft survival rates and induce transplantation tolerance. Most of these studies have used either CTLA4Ig, a fusion protein of CTLA-4 and human Ig that competitively binds CD80 and CD86, or a blocking monoclonal antibody to CD154. Costimulatory blockade has been partially successful in mouse and rat models of cardiac, hepatic, islet, renal, lung, and bone marrow transplantation. Although a single agent alone such as CTLA4Ig or anti-CD154 antibody can improve long-term graft survival rates, these agents by themselves are unlikely to yield indefinite graft survival; late allograft loss resulting from chronic rejection is the rule. Most commonly, either a transfusion of donor-specific lymphocytes or the combination of CTLA4Ig and anti-CD154 is required for long-term survival, with or without tolerance. Furthermore, the results in nonhuman primates are not as good as those in rodent models.

In murine models in which CTLA4Ig and/or anti-CD40 antibody has been used to induce tolerance, it has been shown that concomitant administration of cyclosporine prevents tolerance induction. It seems that the induction of tolerance in T cells deprived of costimulatory signals is an active process involving TCR signaling events that are sensitive to cyclosporine. Therefore, in the presence of cyclosporine, tolerance cannot be achieved by this means. These references therefore teach away from the use of cyclosporine in tolerance induction regimens.

In a protocol in which the combination of CTLA4Ig given 2 d after transplantation and donor-specific lymphocytes is used to induce cardiac allograft tolerance in mice, blockade of CTLA-4 at the time of transplantation prevents tolerance induction and leads to early rejection. Therefore, early CTLA-4 signals may be permissive for some T cell toleragenic/inhibitory strategies; without these signals, it may prove difficult to turn off the immune response. Similarly, in murine models of autoimmune disease, blockade of CTLA-4 exacerbates the duration and severity of the illness. Because agents such as CTLA4Ig prevent CD80 and CD86 from binding to both CD28 and CTLA-4, they have both the potential to block positive signals (through CD28) and the undesired ability to block negative signals (through CTLA-4).

In all of these methods, the tolerance is either unreliably induced, has not been achieved in humans or is not therapeutically or clinically useful. There is a clinical need for methods of preventing immune responses to antigens. The present invention addresses this problem.

SUMMARY OF THE INVENTION

Methods are provided for inducing antigen specific immune tolerance in a mammalian host. A toleragen, which comprises substantially all of the immunogenic epitopes present in the antigen of interest, is administered to a mammalian host over a period of time in combination with a T cell immunosuppressant, at a does sufficient to provide profound immunosuppression. The regimen may further comprise administration of an anti-proliferative agent. In one embodiment of the invention, this tolerizing regimen is preceded by a conditioning period, wherein the T cell immunosuppressant is administered in the absence of the toleragen. After the tolerizing regimen, the host is withdrawn from the immunosuppressive agent, but is able to maintain specific immune tolerance to the immunogenic epitopes present on the toleragen. Maintenance doses of the toleragen are optionally administered after the tolerizing regimen is completed.

The toleragen can be any antigen, particularly soluble protein antigens, e.g. therapeutic proteins, cocktails of transplantation antigens, etc., and may be identical to the antigen of interest, or may be a modified form of the antigen with enhanced toleragenic-properties, for example to increase uptake by non-professional antigen presenting cells. Preferably the toleragen comprises a high uptake moiety, and is taken up efficiently by a widely present high-affinity receptor, e.g. mannose 6-phosphate receptor, etc. Other receptors that are widely present and equal in affinity are also suitable. An antigen without a suitable high uptake capability may be modified to contain a moiety that provides this function to allow uptake by tolerizing cell types.

In one embodiment of the invention the host is immunologically naïve to the antigen of interest, i.e. there is no pre-existing, or memory immune response to the antigen. In another embodiment of the invention the host has been exposed to the antigen. For the latter case it may be necessary to ablate cells of the immune system responsible for the pre-existing immune response.

The invention further contemplates use of a toleragen comprising an antigen and a high uptake moiety, for the manufacture of a medicament for use in combination therapy with a T cell immunosuppressive agent in the prophylactic induction of immune tolerance to the antigen component of the toleragen.

In particular aspects of the present invention, it should be noted that the dose of the immunosuppressive agent is to be sufficient to substantially suppress T cells. Variations in dosage of the drugs may be combined to reach the same degree of T cell suppression in different subjects and under different conditions. The level of T cell suppression is monitored as that level at which the T cells do not proliferate in response to antigen stimulation. Methods for monitoring T cell proliferation are known to those skill in the art, and may be used in conjunction with the present invention.

In preferred embodiments, the range of dose for the antigen/toleragen may be between 0.001 mg/kg to 5 mg/kg/week. More preferably, the dose range of the toleragen is between 0.01 mg to 1 mg/kg and more preferably 0.03 mg/kg/week to 0.1 mg/kg/week. In preferred embodiments, the dose for the antigen/toleragen is 0.056 mg/kg body weight once per week.

In those preferred embodiments in which the immunosuppressive agent is CsA, CsA is given to reach a plasma concentration of >400 ng/ml although 300 ng/ml or greater may also be used. A preferred dose range may be between 1 mg/kg to 30 mg/kg, most preferably in humans the dose range may be between 5 and 15 mg/kg/day. Such a daily dose may be administered by dividing the dose into two, three, four or more fractions of the complete dose, which would be administered at spaced intervals during the day. Alternatively, the dose may be administered as one single dose.

The medicaments of the invention further may comprise a nucleotide analog. In those embodiments in which the analog is azathioprine, the range of dose of this agent may be 1 mg/kg/day to 10 mg/kg/day administered daily or every other day.

Figure 1:
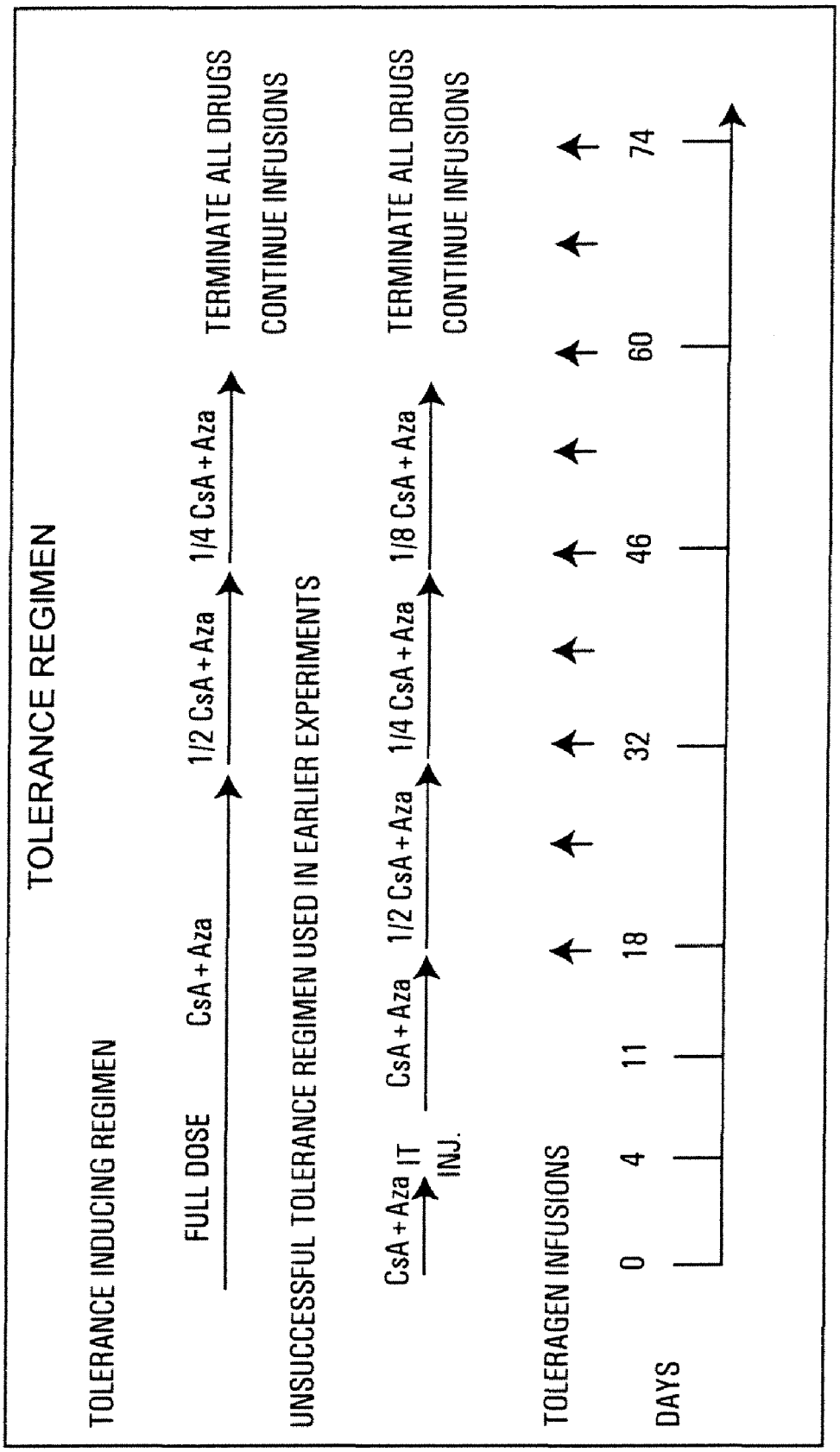
FIG. 1. A diagram of the tolerance regimen is shown. The common example for the tolerance regimen requires only the CsA+Aza treatment (with CsA dose at 25 mg/kg/day) along with toleragen infusions on the schedule shown. Additional treatments indicated such as intrathymic injection and monoclonal antibodies are shown as examples of treatments that did not work or matter to tolerance induction. These non-effective regimens are included in the examples to provide contrast with the response of those canines optimally tolerized to the antigen by the invention.

For the common tolerance regimen, the canines received daily CsA (25 mg/kg/day) plus every other day Aza from day 0 to day 18 as shown on the timeline at the bottom of the figure. Weekly iduronidase enzyme infusions are initiated at day 18 as indicating by the upward arrows above the timeline. The canines then received weekly infusions of toleragen at 0.056 mg/kg/wk. At 2 week intervals thereafter, the CsA+Aza dose was halved, and finally quartered from the initial dose in the final 2 week segment. Drugs CsA+Aza were then terminated after a total 60 days and toleragen infusions continued on a weekly basis.

For non-tolerance inducing regimens, the canines received intrathymic injection or monoclonal antibodies and 25 mg/kg dose of CsA and 5 mg/kg of Aza on alternate days (i.e. each drug on an every other day). On day 4, the canines receive intrathymic injection, if scheduled. In the top protocol diagram for IT+drugs, the canine receives CsA+Aza for 0-4 days, and then receives an intrathymic injection (IT Inj. Or ITI). If monoclonal antibodies are indicated, they are given in the days prior to IT injection. The exact dosing performed depends on the experiment. The CsA and Aza dose administered on alternate days was halved on day 18, the first day that the canine was infused. The canines began receiving 0.56 mg/kg of enzyme on a weekly basis. For the subsequent 2 weeks, the canines received CsA and Aza at ½ the initial doses on alternate days. Thereafter, the drug dose was halved again to ¼ the initial and after a further 2 weeks, it was halved again to $\frac{1}{8}^{th}$ the initial dose. After 2 weeks at $\frac{1}{8}^{th}$ the initial dose, the drugs were terminated and the canine continued to receive weekly infusions of enzyme.

Figure 2:
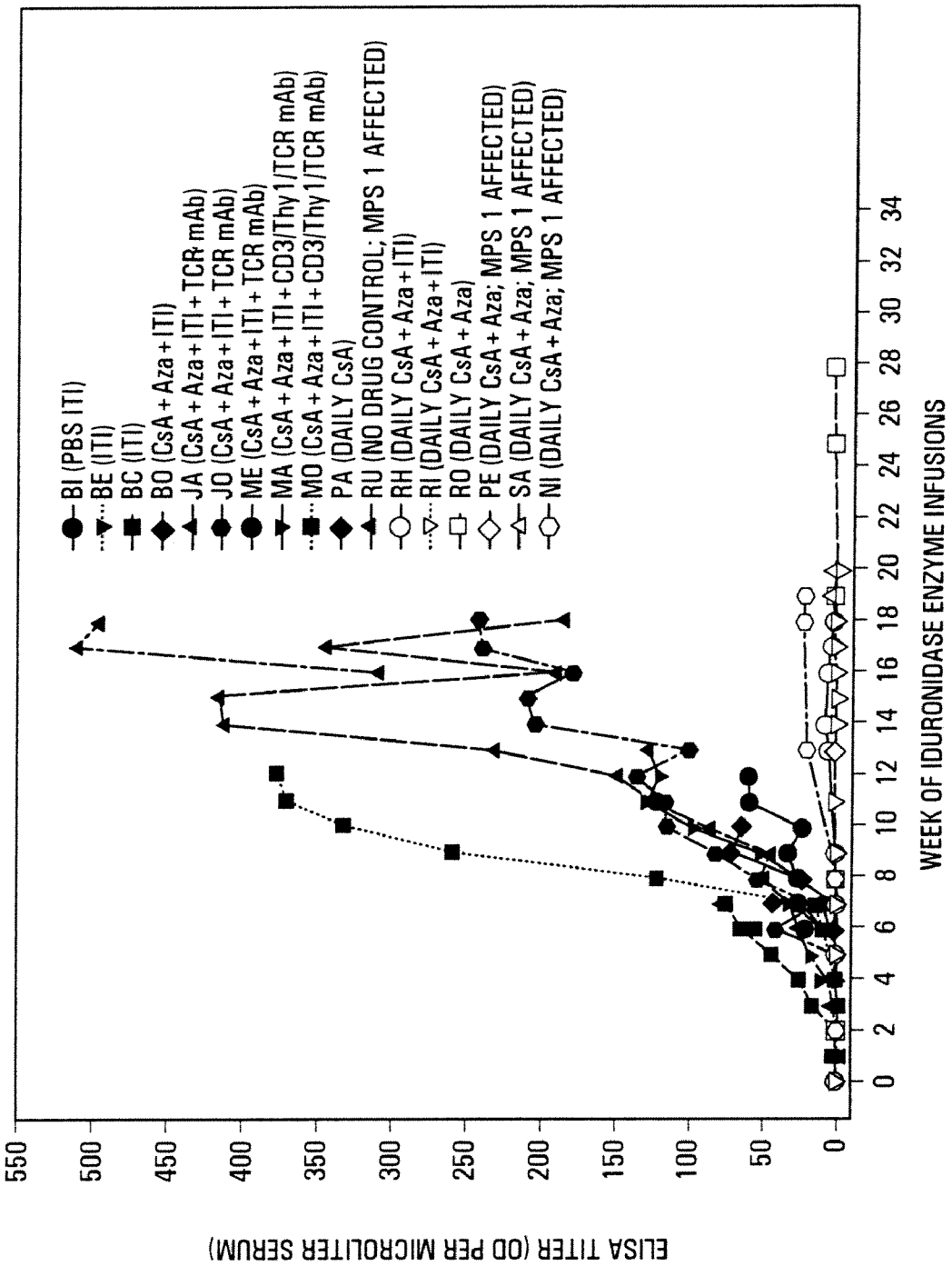

FIG. 2. Induction of tolerance with daily CsA and every other day Aza during infusions of recombinant human iduronidase (rhIDU). In the figure, the antibody titer to iduronidase from 6 tolerant (open symbols) and 11 non-tolerant (closed symbols) canines is shown as OD Units/µL undiluted serum as measured by ELISA is plotted against the week of enzyme infusion. Beginning 18 days before iduronidase infusion, the canines received a tolerance regimen as described in example 1. Beginning at week 1, the canine is infused with weekly intravenous infusions rh-Idu at 0.056 mg/kg/week iduronidase. Low antibody levels (<20 for the iduronidase ELISA) with continued iduronidase challenge indicate tolerance in the dogs receiving the optimal tolerance regimen and titers exceeding 50 and up to 500 indicate an active immune response. The CsA+Aza drug regimen ends at week 7 of enzyme challenge and low antibody response beyond that point indicates that the tolerance is not dependent on continued immune suppression.

Figure 3:
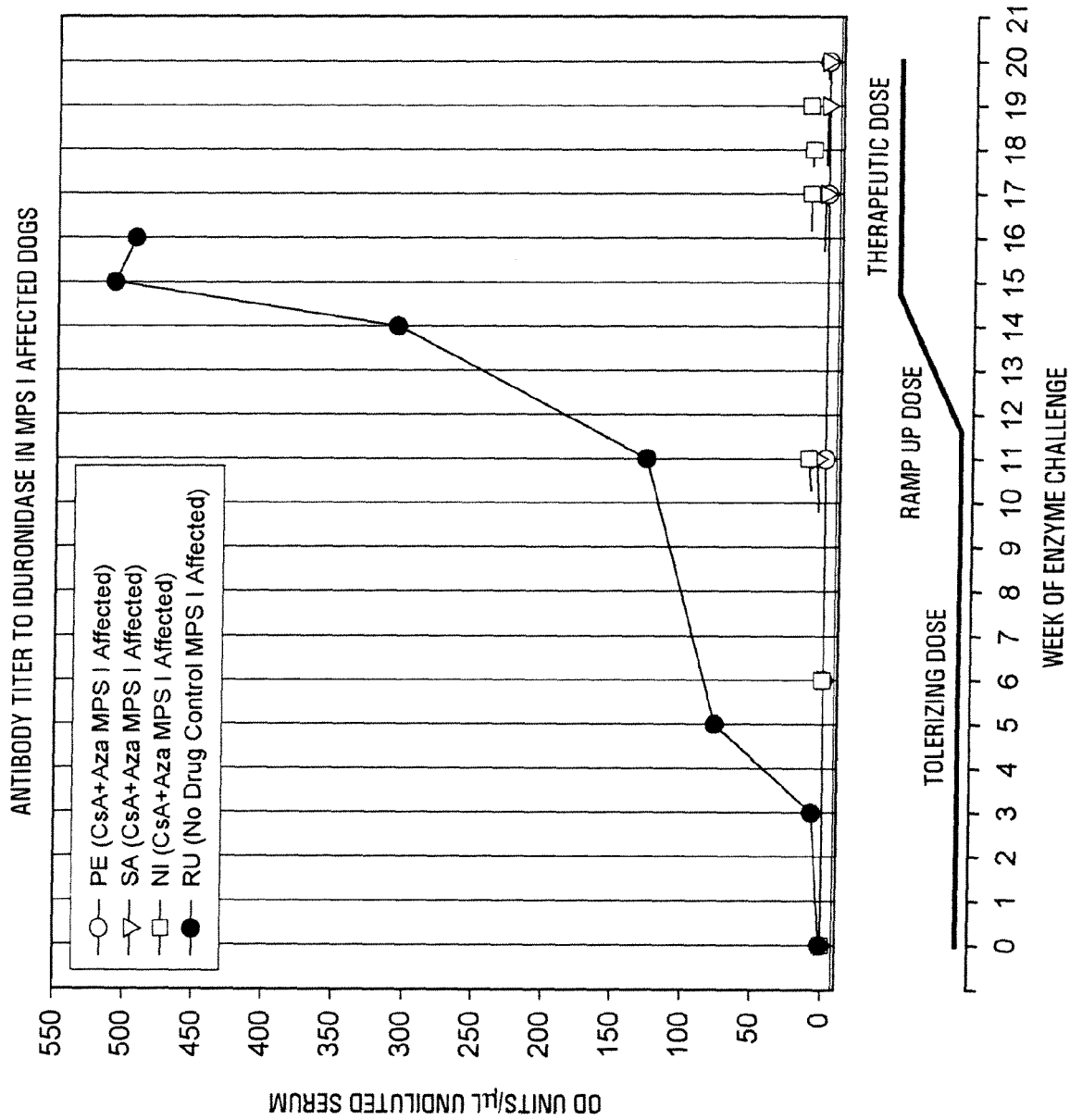

FIG. 3. Successful induction of tolerance in iduronidase-deficient MPS I dogs and tolerance to subsequent high therapeutic levels of enzyme. Three MPS I dogs were tolerized using the tolerance regimen and one MPS I dog served as a control and did not receive the tolerance regimen. The antibody titer to iduronidase in the three tolerant MPS I dogs (open symbols) and 1 non-tolerant (closed symbol) MPS I dog is shown with OD Units/µL undiluted serum as measured by ELISA plotted versus the week of enzyme challenge. The tolerant canines received the Tolerance Drug Regimen as described in example 2; the non-tolerant control received no drug treatment. Low antibody levels (<20 OD) with continued antigen challenge indicate tolerance. The tolerizing drug regimen ends at week 7 of enzyme challenge and low antibody levels beyond that point is indicative of induced tolerance. The 4 canines received 0.056 mg/kg/week intravenous iduronidase infusions at weeks 1-12. Subsequently, the canines received a stepwise increase in iduronidase dose over 3 weeks to therapeutic doses of 0.500 mg/kg/week at week 15 of enzyme challenge. Antibody levels in tolerant canines remained <20 OD Units at week 15 compared to control RU antibody levels of >500 OD Units at week 15 in response to increasing iduronidase antigen dose. At week 16, non-tolerant canine RU had a serious clinical anaphylactic reaction during the infusion and treatment was ended. The tolerant canines did not exhibit anaphylaxis during the infusions.

Figure 4:
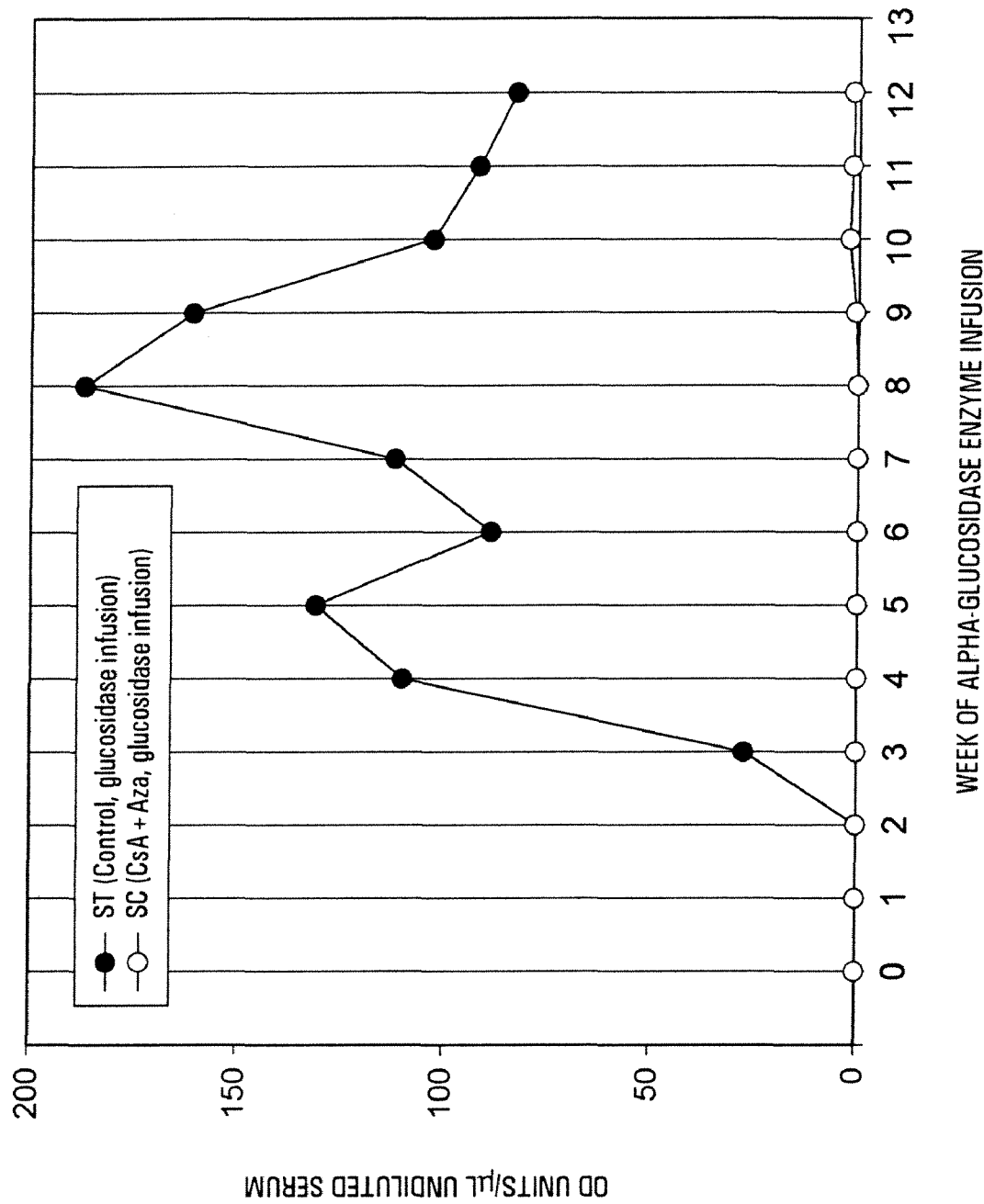

FIG. 4. Successful induction of antigen-specific tolerance to rhGAA, a second lysosomal enzyme being developed to treat Pompe disease. The antibody titer to rh-alpha-glucosidase (rhGAA) for 1 tolerant (SC, open symbol) and 1 non tolerant (ST, closed symbol) canine is shown as OD Units/µL undiluted serum as measured by ELISA versus the week of enzyme challenge. The tolerant canine received the tolerance drug regimen as described in the example 3. At week 1, the canine is tolerized with weekly intravenous infusions of rhGAA at 0.056 mg/kg/week. The cyclosporine and azathioprine (CsA(daily)+Aza) is continued and then the dose halved every 2 weeks until the canine is off drugs at week 7 of enzyme challenge. The non tolerant control received no drug treatment. The tolerizing drug regimen ends at week 7 of enzyme challenge and low antibody levels beyond that point is indicative of induced tolerance that is maintained in the absence of continued immune suppression. The 2 canines received 0.056 mg/kg/week intravenous rhGAA infusions at weeks 1-12. Antibody levels in the tolerant canine remained <5 OD Units at the highest point compared to the non tolerant control antibody levels of >150 OD Units at the highest point. The result confirms that the tolerance regimen can succeed with another high uptake immunogenic enzyme with therapeutic implications.

Figure 5:
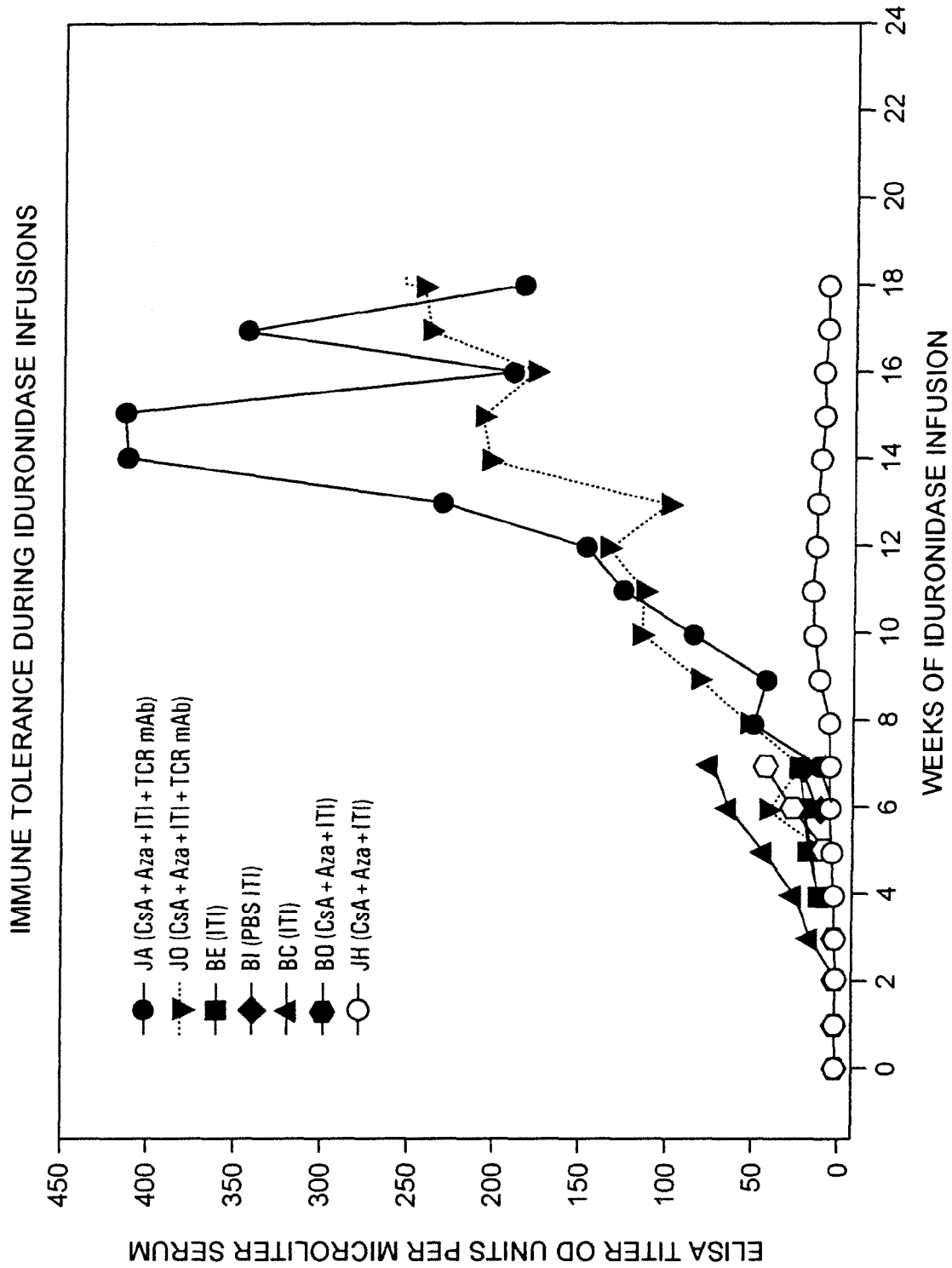

FIG. 5. Data from 6 non-tolerant canines is shown compared with one canine (JH) who became tolerant. The non-tolerant canines have ELISA titers exceeding 50 and in some cases exceeding 200 OD U/µl/serum. In contrast, JH had an antibody titer of less than 20 OD U/µl/serum throughout 18 weeks of iduronidase infusions. JH was distinguished by cyclosporine levels of greater than 500 ng/ml in blood, while the other canines were less than 400 ng/ml in blood and often less than 200 ng/ml in blood.

Figure 6:
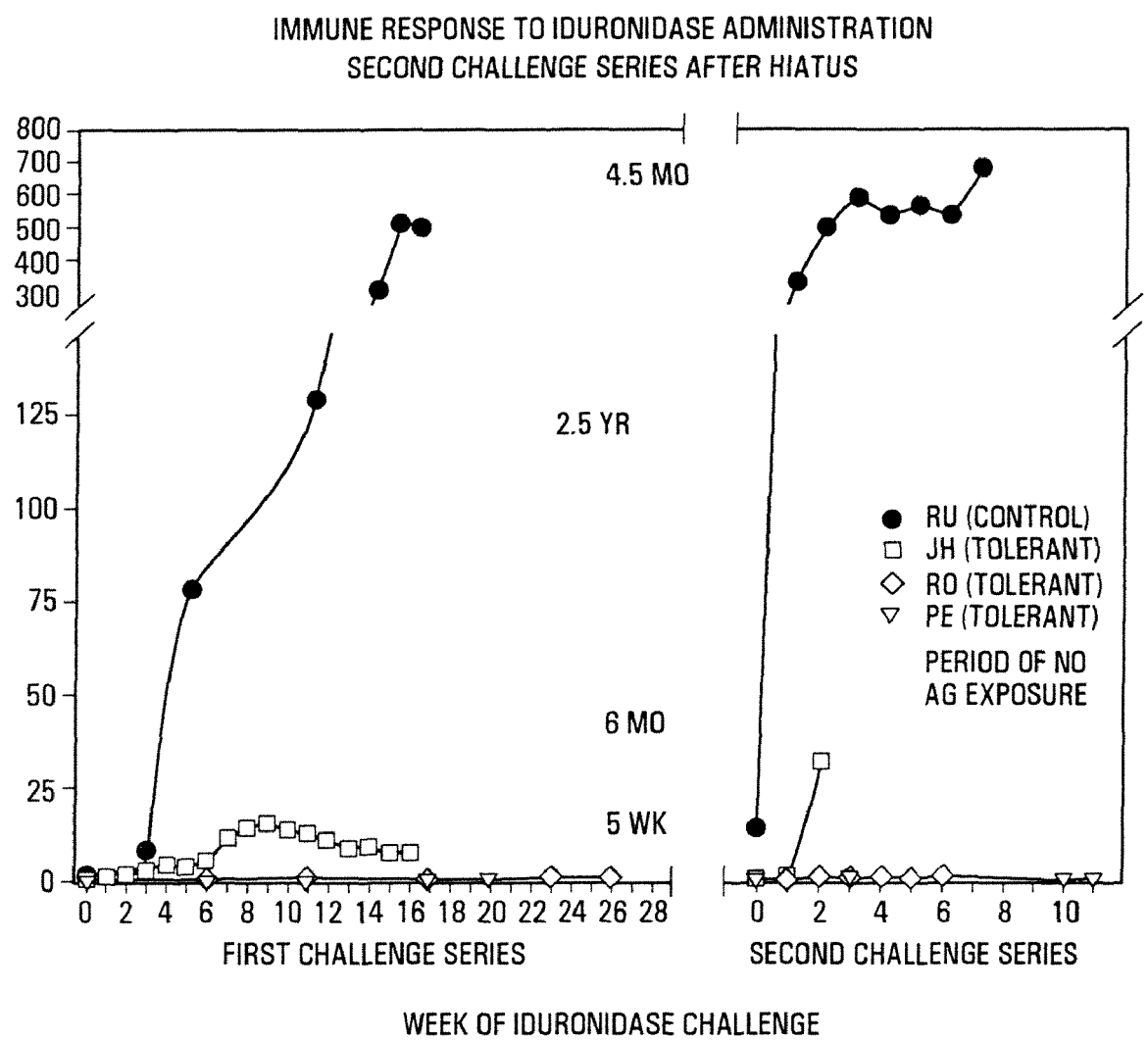
Figure 7A:
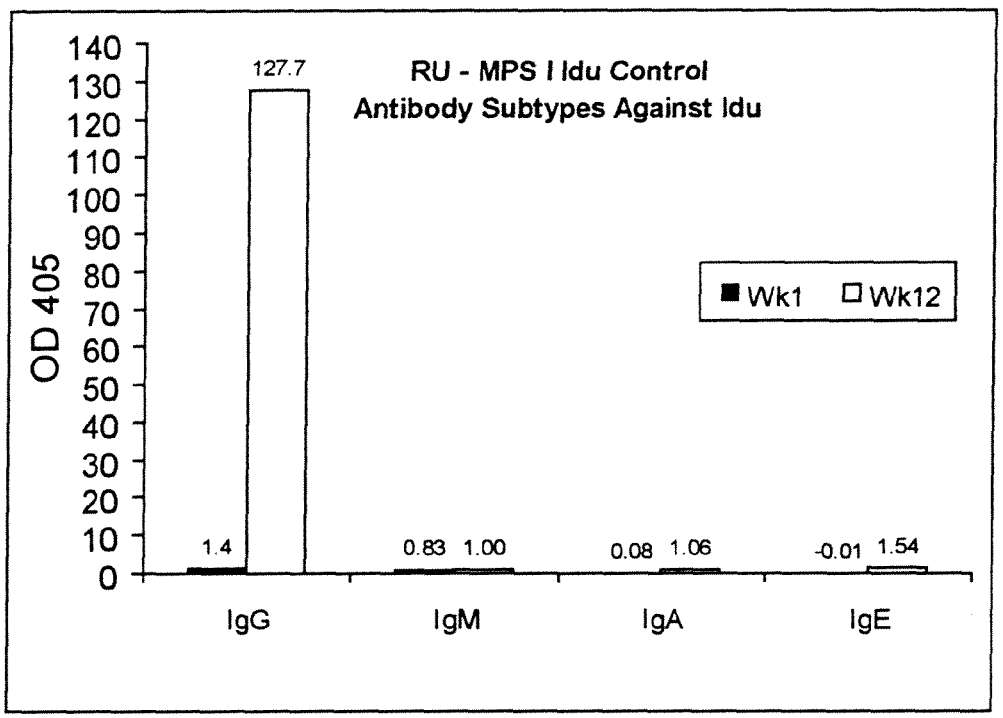
Figure 7B:
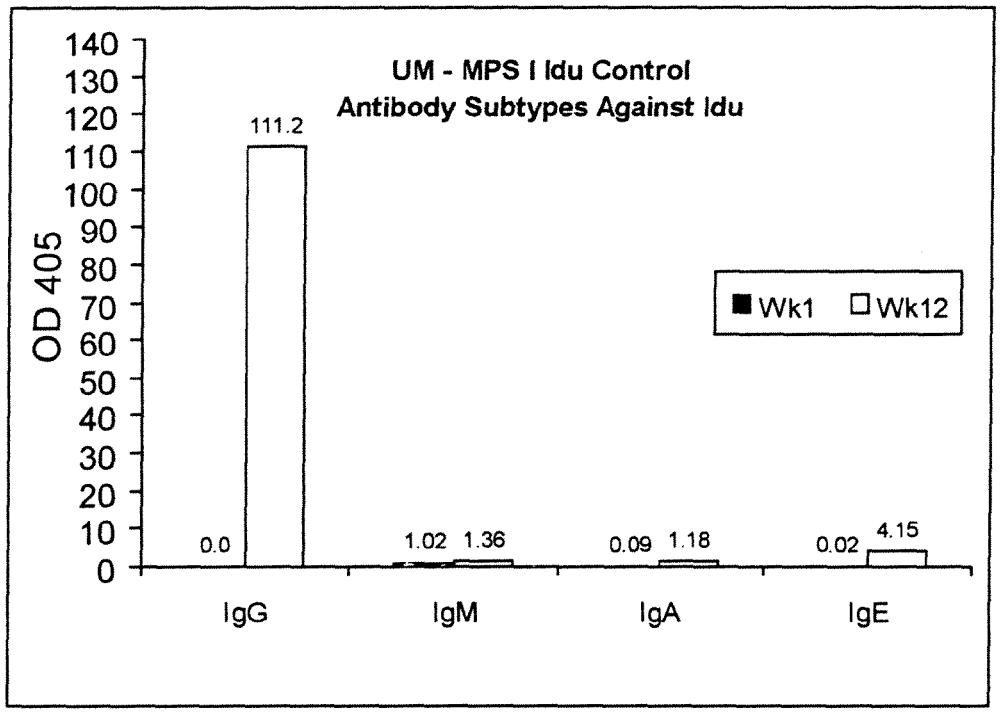
Figure 7C:
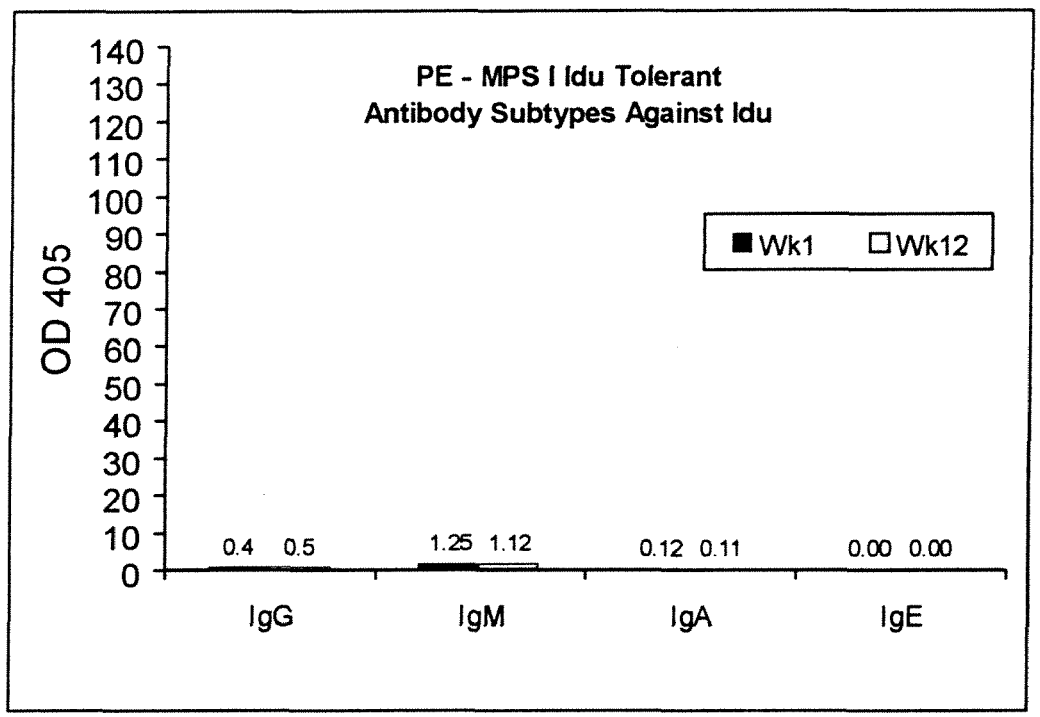
Figure 7D:
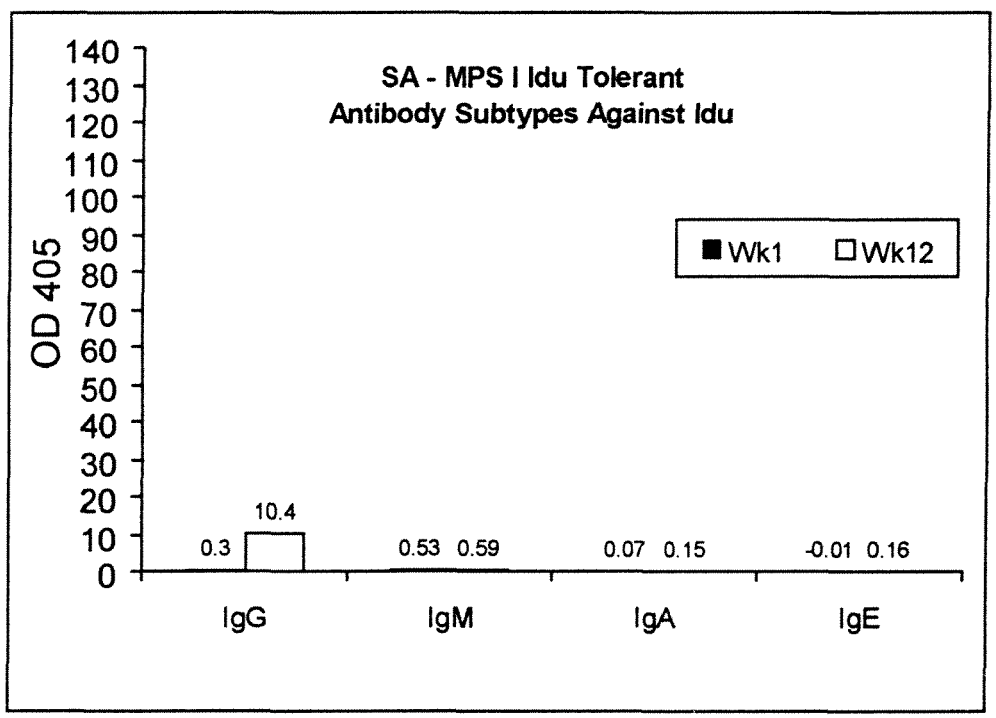

FIG. 6. Antigen-specific tolerance is long-lasting. The figure shows the antibody titer of canines tolerized (JO, RO) and not tolerized (RU) over time. In the first segment, the titer during and after tolerization is shown. RU has a high titer, whereas the other canines have a low titer. After gaps in time of 5 weeks, 4.5 mos, 6 mos or 2.5 years, the canines were rechallenged with iduronidase. Tolerant dogs (PE, RO) showed no immune response to the iduronidase even after 5 weeks to 6 months of hiatus from toleragen infusions. The non-tolerant canine RU, showed a response to antigen of >20 fold after only 2 doses of enzyme challenges following a 4.5 months hiatus. The original tolerant dog JH shows a partial response after 2.5 years of hiatus. The data show a long-lasting effect of the induced tolerant state.

FIG. 7. Tolerance regimen prevents the induction of other Ig subtypes, in addition to IgG. FIGS. 7A and 7B show ELISA titers of non-tolerant control dogs before and after 12 weekly infusions with iduronidase. FIGS. 7C and 7D show ELISA titers of tolerant control dogs before and after 12 weekly infusions with iduronidase.

Figure 8:
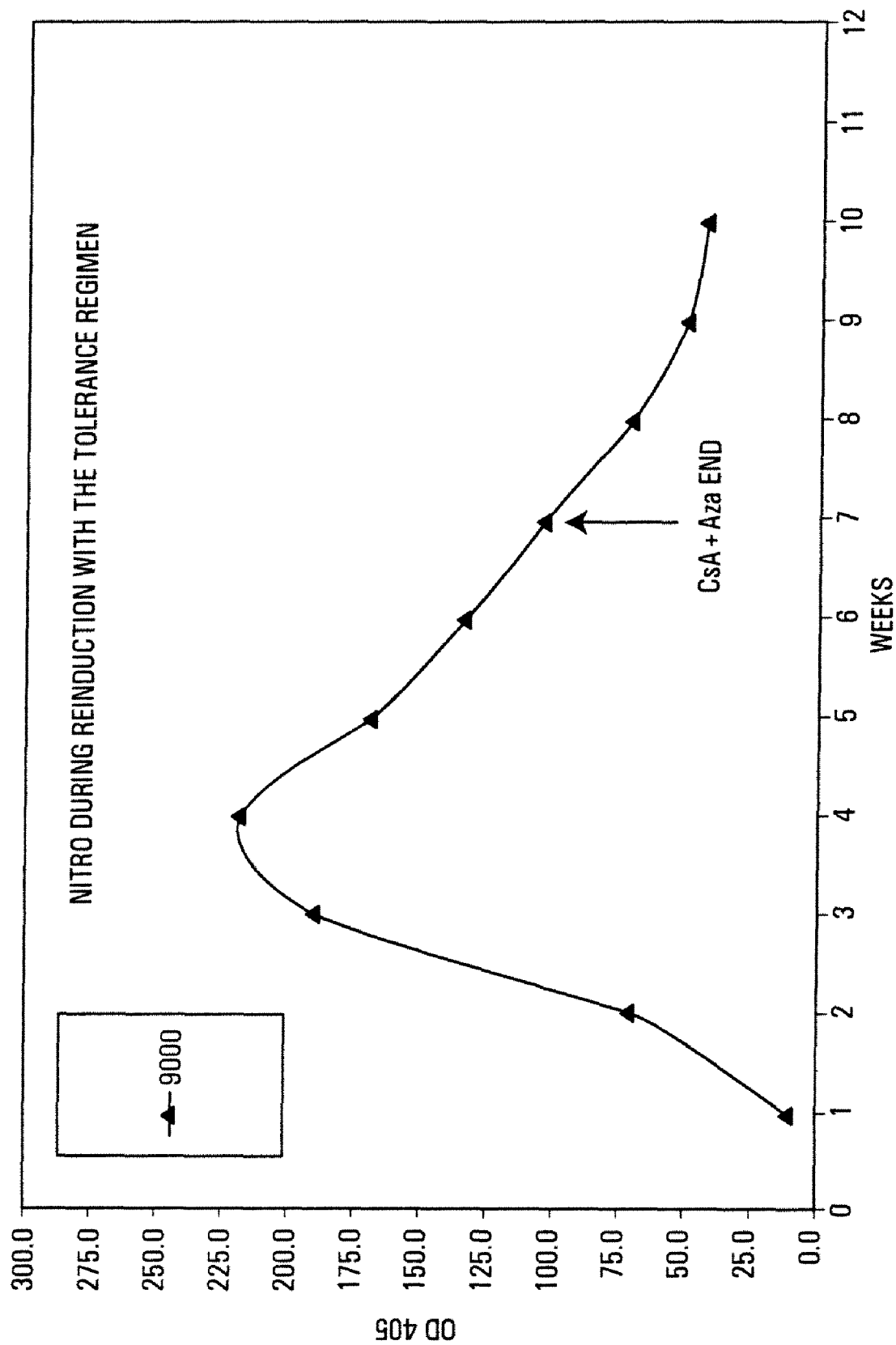

FIG. 8. Tolerance regimen may be used to induce relative tolerance or reduce Ig titer with the regimen in canines with pre-existing immune response. Nitro was allowed a 6-month hiatus from antigen exposure. Upon reexposure to antigen after this period, the IgG titer initially rose during the administration of the CsA+Aza regimen to greater than 100 in a typical anamnestic response and than rapidly fell to below 20. The immune response was reduced by the reinduction of tolerance using the combined tolerization regimen.

Figure 9:
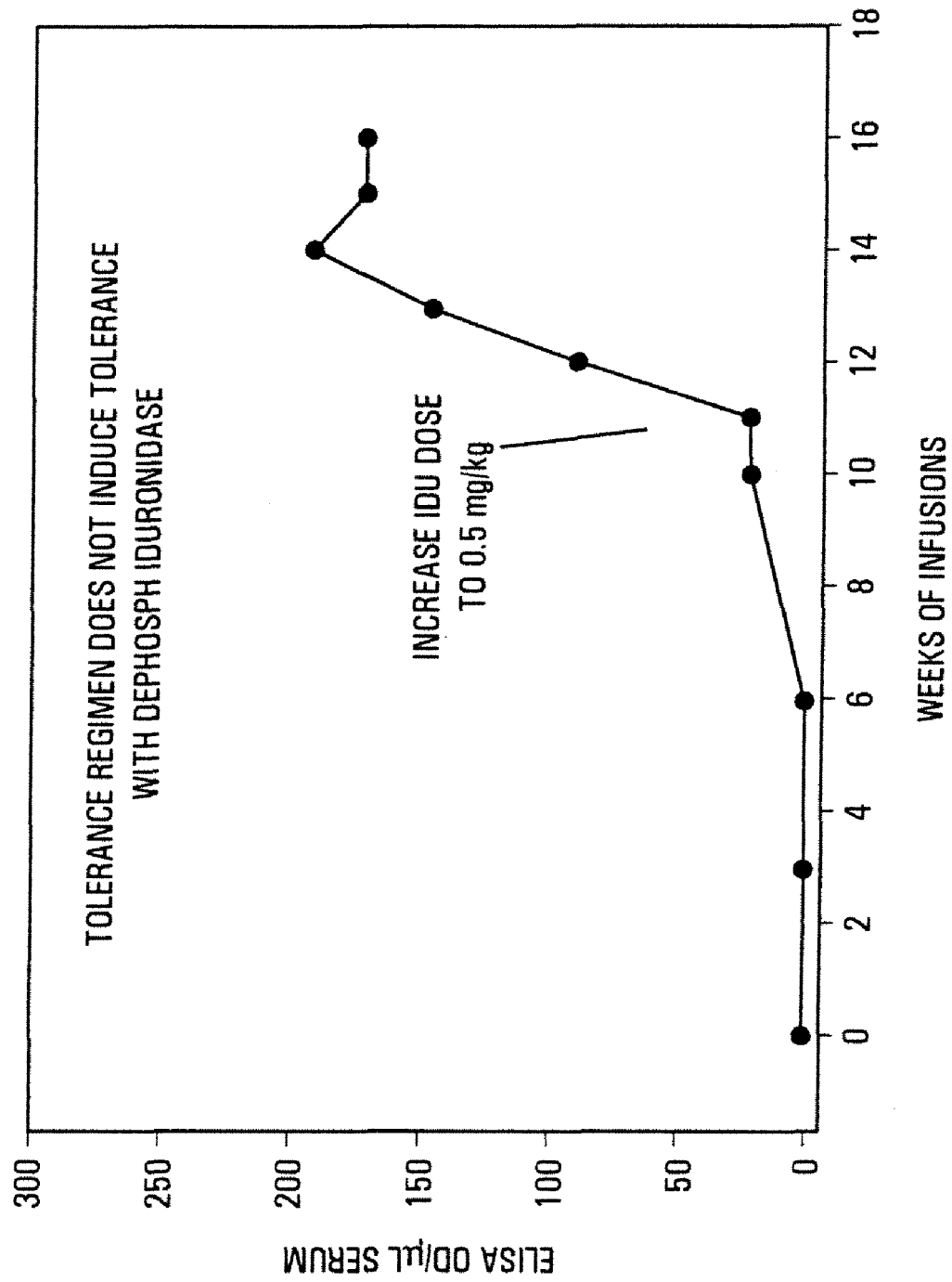

FIG. 9. Confirmation that high uptake moiety of iduronidase (the mannose 6-phosphate group) is required for immune tolerance with iduronidase. To show that an M6P high uptake moiety assists in the induction of tolerance to antigen, recombinant iduronidase was dephosphorylated by incubation with acid phosphatase bound to beads. The dephosphorylated iduronidase enzyme was applied with the tolerance regimen (CsA+Aza) to canines. The study showed that the canine treated with dephospho iduronidase was not tolerized to iduronidase, thereby suggesting that high uptake affinity (the mannose 6-phosphate moiety) is needed for tolerance.

DETAILED DESCRIPTION OF THE EMBODIMENTS

Antigen specific immune tolerance is induced in a mammalian host by administration of a toleragen in combination with a regimen of immunosuppression for a period of time sufficient to tolerize the host. Immunosuppression is accomplished by administration of a T cell immunosuppressive agent. The methods may further comprise administration of an anti-proliferative agent. The methods optionally include a conditioning period preceding the administration of the toleragen, where the immunosuppressive agent is administered in the absence of the toleragen. After the tolerizing regimen, the host is withdrawn from the immunosuppression, but is able to maintain specific immune tolerance to the immunogenic epitopes present on the toleragen. Maintenance doses of the toleragen may be administered after the tolerizing regimen is completed.

In one embodiment of the invention the host is immunologically naive to the antigen of interest, i.e. there is no pre-existing, or memory immune response to the antigen. In another embodiment of the invention the host has been exposed to the antigen. The latter case it may be necessary to ablate cells of the immune system responsible for the pre-existing immune response. The inventors have shown that the tolerance regimen of the present invention may be used to induce relative tolerance or reduce immunoglobulin titer in canines with pre-existing immune response against a given antigen.

The methods are useful in the proactive establishment of tolerance where a protein or other immunogenic agent is to be administered to a naive host. For example, the administration of therapeutic antibodies, of growth factors, enzymes, and other polypeptides not previously present in the host can give rise to a significant immune response, which diminishes the effectiveness of the treatment. By proactive establishment of tolerance, the long term effectiveness of such treatment is enhanced. The methods of the invention also find use in establishing tolerance prior to transplantation; and in the treatment of autoimmune diseases.

In exemplary studies, the inventors demonstrated that a method to reduce or prevent a clinically significant antigen-specific immune response to recombinant human α-L-iduronidase (rhBDU) used to treat canine mucopolysaccharidosis I (MPS I). The method employ an initial 30-60 day regimen of a T-cell immunosuppressive agent such as cyclosporin A (CsA) and an antiproliferative agent, such as, azathioprine (Aza), combined with weekly intravenous infusions of low doses of rhIDU. The typical strong IgG response to weekly infusions of rhIDU in canines was greatly reduced or prevented using a 60 day regimen of immunosuppressive drugs, cyclosporin A (CsA) and azathioprine (Aza), combined with weekly intravenous infusions of low doses of rhIDU. More specifically, using the regimen, eight canines had a 20-fold reduction in antibody titer after 12 weekly infusions of rhIDU (6 weeks without CsA+Aza) and low titers did not increase with further rhIDU infusions up to 6 months and full therapeutic rhIDU doses (the eight normal and MPS I canines had a mean antibody titer of 7.2 OD units/µl serum by ELISA compared to 149 OD units/µl in eight control canines). The canines tolerated higher therapeutic doses of iduronidase for up to 6 months without an increase in titer (mean of 7.5 OD/µl serum, n=6) whereas immune responsive canines had further 2-3 fold increases in antibody titer (mean of 369 OD/µl serum, n=2). Antiserum from immune responsive canines inhibited cellular uptake of iduronidase in vitro by >95% whereas antiserum from non-responsive canines did not. The data suggest that a simple protocol can prevent or reduce the clinically significant immune response to lysosomal enzyme replacement therapy, as well as reducing the immune response to other clinically significant antigens.

The studies demonstrated that one key factor determining success of the tolerizing regimen was a high serum trough level of CsA of preferably >400 ng/ml. In addition, the studies of the tolerizing antigen demonstrated that high-affinity, mannose 6-phosphorylated (M6P) enzymes (rhIDU, alpha-glucosidase) can act as toleragens whereas the non-phosphorylated protein ovalbumin could not. High affinity M6P makers appear essential since dephosphorylated rhIDU did not allow induction of the tolerant state. A model is proposed in which tolerance is induced under conditions in which all T cell activation is suppressed by CsA+Aza, while immature and non-professional antigen presenting cells (APC) are efficiently loaded with antigen via the M6P receptor and inactivate antigen-responsive T cells or activate regulatory T cells to induce a tolerant state in the canines. Methods and compositions for exploiting these discoveries are discussed in further detail herein below.

DEFINITIONS

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Antigen. As used herein, the term antigen is intended to refer to a molecule capable of eliciting an immune response in a mammalian host, particularly a humoral immune response, i.e. characterized by the production of antigen-specific antibodies. Antigens of interest are therapeutic agents, e.g. polypeptides, and fragments thereof; autoantigens, e.g. self-polypeptides; transplantation antigens; and the like. In response to antigens, antibodies are produced in a variety of classes, subclasses and isotypes.

The portion of the antigen bound by the antibody is referred to as an epitope. Antigens, particular complex antigens such as polypeptides, usually comprise multiple epitopes. Where the antigen is a protein, linear epitopes range from about 5 to 20 amino acids in length. Antibodies may also recognize conformational determinants formed by non-contiguous residues on an antigen, and an epitope can therefore require a larger fragment of the antigen to be present for binding, e.g. a protein domain, or substantially all of a protein sequence. It will therefore be appreciated that a therapeutic protein, which may be several hundred amino acids in length, can comprise a number of distinct epitopes.

The level of affinity of antibody binding that is considered to be "specific" will be determined in part by the class of antibody, e.g. antigen specific antibodies of the IgM class may have a lower affinity than antibodies of, for example, the IgG classes. As used herein, in order to consider an antibody interaction to be "specific", the affinity will be at least about $10^{-7}$ M, usually about $10^{-8}$ M to $10^{-9}$ M, and may be up to $10^{-11}$ M or higher for the epitope of interest. It will be understood by those of skill in the art that the term "specificity" refers to such a high affinity binding, and is not intended to mean that the antibody cannot bind to other molecules as well, or that some minor cross-reactivity to an epitope may not be present in the host.

Antigen specific immune tolerance. For the purposes of the present invention, tolerance is the absence of an immune response to a specific antigen in the setting of an otherwise substantially normal immune system. Tolerance is distinct from generalized immunosuppression, in which all, or all of a class such as B cell mediated immune responses, of immune responses are diminished.

Therapeutic antigen specific immune tolerance provides a specific state in a host, where a therapeutic molecule of interest, e.g. a therapeutic protein, can be administered multiple times at the normal effective dose. When such antigen specific tolerance absent, successive administration of a normal dose of the therapeutic agent leads to decreased efficacy, due to antibody interference with the therapeutic agent, and therefore the amount of the agent required for an effective dose will increase. When antigen specific immune tolerance is achieved according to the methods of the present invention, the amount required for an effective dose of a therapeutic agent will increase by not more than about five fold after successive administration, usually by not more than about 2.5 fold after successive administration, and may not be increased above the initial dose.

Alternatively or in combination with the efficacy benefit described above, the immune tolerance state provides for an increase in the safety of therapeutic protein or other drug administration. Immune responses to drugs can cause anaphylaxis or anaphylactoid or immune complex reactions based on the production of specific antibodies when tolerance is absent. The decreased or absent immune response observed in the presence of tolerance according to the methods of the present invention, will also decrease and limit the decreased safety of administration of such drugs due to a decreased antibody mediated adverse events.

Where the antigen of interest is an autoantigen, the induction of antigen specific immune tolerance will be sufficient to decrease the symptoms of the autoimmune disease in the patient, for example a patient may be sufficiently improved so as to maintain normal activities in the absence, or in the presence of reduced amounts, of general immunosuppressants, e.g. corticosteroids.

Where the antigen of interest is one or more transplantation antigens, the induction of antigen specific immune tolerance permits the transplanted organ to survive and function in the recipient host in the absence, or in the presence of reduced amounts, of general immunosuppressants.

An alternative method for determining antigen specific immune tolerance is to observe the presence of antigen-specific antibodies in the serum of the host animal after successive administration of the therapeutic agent. In a non-tolerant host, the titer of antibodies specific for an antigen, e.g. a therapeutic agent, autoantigen, transplantation antigen, etc. will increase by many orders of magnitude on successive administration, or exposure. For example, it is shown herein that specific antibody titers can rise more than about 50 fold after about 8 weeks of successive administration of a therapeutic protein, often more than 100 fold, and over time may increase by as much as 1000 fold or more. In a tolerant host, the rise in specific antibody titer will be not more than 10% of the increase for a corresponding non-tolerant host, and may be not more than about 5% of the increase. For example, an increase of less than 50 fold in the specific antibody titer may be observed over a period of from about 8 weeks, to several months. The specific level of increase observed against a particular agent vary depending on the nature of the agent, prior exposure of the host to the agent, the mode by which the agent is administered, the method by which the response is measured and the like. Methods are well known in the art for determining the presence of a specific antibody in patient serum, e.g. RIA, ELISA, etc., and do not need to be elaborated here.

Another aspect of tolerance is the presence of an otherwise substantially normal immune system. The methods of the present invention are not directed to a general immunosuppression, and after the tolerizing regimen the immune response to antigens other than the antigen of interest are substantially normal, usually reduced by not more than about five fold as compared to an untreated control, more usually reduced by not more than about two fold as compared to an untreated control, and may be undistinguishable from a normal response.

Mammalian species that may benefit from the methods of the invention include canines; felines; equines; bovines; ovines; etc. and primates, particularly humans. Animal models, particularly small mammals, e.g. murine, lagomorpha, etc. may be used for experimental investigations. Animal models of interest include those for models of therapeutic protein administration, autoimmunity, graft rejection, and the like.

Toleragen comprising a high uptake moiety. Toleragen is the form of the antigen of interest that is administered to the host during the tolerizing regimen, and will comprise substantially all of the epitopes present in the antigen, which epitopes may be provided as one or a cocktail of agents. In some cases the toleragen and the antigen will be identical, but they may also differ in the presence of modifications, formulations, and the like. Toleragens are administered in soluble form, i.e. substantially free of aggregates, and in an acellular form, while the antigen of interest may not be soluble. Toleragens may also comprise carriers to enhance interaction with the immune system, may comprise multiple fragments derived from the antigen of interest; may by conjugated to groups that increase toleragenicity, may be fusion proteins comprising polypeptide moieties of interest, and the like.

The toleragens either comprise or are conjugated covalently to a high uptake moiety. High uptake moieties are polypeptides that are widely recognized and internalized by receptors present on non-professional antigen presenting cells. Preferably a receptor is chosen that is widely expressed on peripheral and central cells that are tolerizing when they present antigen, and which is not exclusively expressed on macrophages, dendritic cells, or other professional antigen presenting cells. Cells that tolerize when presenting antigens include, for example, liver sinusoidal endothelial cells, cortical/medullary thymic epithelium cells, and similar cell types.

It is especially preferred that the receptor has a $K_{uptake}$ for the ligand of at least about $10^{-6}$ M, usually at least about $10^{-7}$ M more usually at least about $10^{-8}$ M and preferably at least about $10^{-9}$ M where $K_{uptake}$ represents the concentration of ligand at which half maximal uptake occurs in a cell. Receptors of interest include the transferrin receptor, the melanotransferrin receptor, mannose 6-phosphate receptor, growth hormone receptor, and the like. Cognate ligands include: insulin-like growth factor II (IGF2), transferrin, growth hormone, insulin, and binding fragments thereof, particularly polypeptides having specific and high affinity receptors on diverse cell types. Single chain antibodies and binding agents from randomized phage display systems could be used if they have adequate affinity for the receptor. To determine the $K_{uptake}$ of a ligand and receptor combination, methods known in the art may be used, for example see Kakkis et al. (1994) *Protein Expr Purif* 5(3):225-32 for assays used to determine the $K_{uptake}$ of alpha-L-iduronidase. The disclosed methods are readily adapted to any ligand and receptor combination. Such assays are also useful in verifying the uptake of toleragens comprising exogenous high uptake moieties.

Where the antigen is a polypeptide taken up by such receptors, the antigen and the toleragen may be identical. Where the antigen of interest is a polypeptide that is not widely taken up by non-professional antigen presenting cells, the toleragen may be a modified form of the antigen, e.g. may be a conjugate of the antigen and a high uptake moiety (ligand), such as mannose 6-phosphate, transferrin, etc.

Alternatively the toleragen may be a modified form of the antigenic polypeptide, comprising amino acid changes, e.g. substitutions, deletions, additions, and the like, which provide the polypeptide with sequences for high uptake. For example, glycosylation motifs may be added or altered, in order to provide suitable post-translational modifications, e.g. a motif for addition of mannose 6 phosphate (see Cantor et al. (1992) *J Biol Chem* 267(32):23349-56). In one embodiment of the invention the toleragen is a fusion protein comprising (a) all or a part of the antigen of interest and (b) a fragment of a protein having a high uptake moiety, where the fragment is sufficient to confer the high uptake properties. For example, a fragment of α-L-iduronidase comprising the necessary motifs for post-translational glycosylation and addition of mannose 6 phosphate may be fused to an antigen of interest.

Methods of conjugating chemical groups to a polypeptide are well known in the art. Chemical groups that find use in linkage include carbamate; amide (amine plus carboxylic acid); ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), disulfide; hydrazone, lipids, and the like, as known in the art. Ester and disulfide linkages are preferred if the linkage is to be readily degraded in the cytosol after transport of the substance. Illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, NHS-PEG-MAL; succinimidyl 4-[N-maleimidomethyl]cyclohexane-1-carboxylate; 3-(2-pyridyldithio)propionic acid N-hydroxysuccinimide ester (SPDP); N,N'-(1,3-phenylene) bismaleimide; N,N'-ethylene-bis-(iodoacetamide); or 4-(N-maleimidomethyl)-cyclohexane-1-carboxylic acid N-hydroxysuccinimide ester (SMCC); m-maleimidobenzoyl-N-hydroxysuccinimide ester (MBS), and succinimide 4-(p-maleimidophenyl) butyrate (SMPB), an extended chain analog of MBS. The succinimidyl group of these cross-linkers reacts with a primary amine, and the thiol-reactive maleimide forms a covalent bond with the thiol of a cysteine residue.

Suppressive Agents

T cell immunosuppressive agent. T cell immunosuppressive agents are compounds that inhibit the activity of T cells, particularly T helper cells, usually without general suppression of the proliferation and activity of other cells, such as B cells, monocytes, bone marrow hematopoietic progenitors cells, etc. Methods of assaying for T cell immunosuppression are well known in the art, include in vitro assays such as release of IL-2 by T helper cells in the presence of antigen, incorporation of $^3$H thymidine into DNA in the presence of antigen or a stimulant such as Con A, release of $^{51}$Cr in the presence of allogeneic stimulatory cells, etc. In vivo assays may rely upon measuring the proliferation of T cells, the release of cytokines, inability to reject a graft while actively suppressed, and the like.

A group of compounds of particular interest for these purposes are the immunophilins, also referred to as calcineurin inhibitors, which inhibit T helper cells. Calcineurin is a $Ca^{2+}$/calmodulin-dependent S/T protein phosphatase 2B, which has been reported to be important in the calcium signaling pathway. This enzyme is a heterodimer of a 61 kDa calmodulin-binding catalytic subunit (calcineurin A) and a small (19 kDa) regulatory subunit (calcineurin B). The immunosuppressive drugs, cyclosporin A, rapamycin, FK506, etc. inhibit calcineurin, which is necessary for the nuclear import of NF-AT (nuclear factor of activated T cells). The dose of T cell immunosuppressive agent for the purpose of tolerization may be higher than that normally used for general immunosuppression, as will be discussed in detail below.

Immunophilins may be administered in a manner as is conventionally practiced. See, e.g., Goodman and Gilman's *The Pharmacological Basis of Therapeutics*, 7th Ed, 1985, p. 1299. For example, CSA may be provided as an oral solution of 100 mg/ml with 12.5% alcohol, and for intravenous administration as a solution of 50 mg/ml with 33% alcohol and 650 mg of polyoxyethlated castor oil. When administered intravenously, CSA may be given as a dilute solution of 50 mg to 20-100 mg of normal saline or 5% dextrose in water, by slow infusion over a period of several hours. The intravenous dose is typically one third of the oral dose. Most preferably, administration of CSA is orally, either in capsule or tablet form. Such formulations may be prepared by any suitable method of pharmacy which includes the step of bringing into association the active compound and a suitable carrier (which may contain one or more accessory ingredients). In general, the formulations can be prepared by uniformly and intimately admixing the active compound with a liquid or finely divided solid carrier, or both, and then, if necessary, shaping the resulting mixture. The preparation of CSA is disclosed in U.S. Pat. No. 4,117,118. CSA which may be used in the practice of the invention is commercially available under the name SANDIMMUNE® from Sandoz Pharmaceuticals Corporation. FK506, also known as tacrolimus, is commercially available under the trade name PROGRAF® from Fujisawa Healthcare. Rapamycin, also known as sirolimus is commercially available under the trade name RAPAMUNE® from Wyeth-Ayerst Pharmaceuticals Inc.

Antiproliferative agent. Antiproliferative agents, for the purposes of the methods of the present invention, are pharmaceutically active compounds that depress cellular proliferation. As the cells of the immune system are often actively dividing, even general anti-proliferative agents frequently have an immunosuppressive effect. Many such anti-proliferative drugs are known in the art, for example as used in chemotherapy.

Anti-proliferative drugs of interest include antimetabolites, e.g. nucleotide analogs such as azathioprine, 6-mercaptopurine, thioguanine, cytarabine, etc.; other analogs, such as methotrexate, mycophenolic acid, or 6-(1,3-Dihydro-4-hydroxy-6-methoxy-7-methyl-3-oxy-5-isobenzofuranyl)-4-methyl-4-hexanoic acid, and the like. Although less preferred, alkylating agents such as cyclophosphamide, chlorambucil, etc. may also find use as immunosuppressive antiproliferatives, for example where there is a pre-existing immune response to the antigen of interest.

In one embodiment of the invention, the antiproliferative agent is azathioprine (AZA) or 6-mercaptopurine (6-MP). As used herein, the term "6-mercaptopurine drug" or "6-MP drug" refers to any drug that can be metabolized to an active 6-mercaptopurine metabolite that has therapeutic efficacy. Exemplary 6-mercaptopurine drugs as defined herein include 6-mercaptopurine (6-MP) and azathioprine (AZA). Other 6-MP drugs include, for example, 6-methylmercaptopurine riboside and 6-TG. 6-TG is a particularly useful 6-MP drug in patients having high TPMT activity. Patients exhibiting high TPMT activity are expected to more easily convert 6-MP drugs such as 6-MP and AZA to 6-MMP. As used herein, the term "6-thioguanine" or "6-TG" refers to 6-thioguanine or analogues thereof, including molecules having the same base structure, for example, 6-thioguanine ribonucleoside, 6-thioguanine ribonucleotide mono-, di- and tri-phosphate, 6-thioguanine deoxyribonucleoside and 6-thioguanine deoxyribonucleotide mono-, di, and triphosphate. The term "6-TG" also includes derivatives of 6-thioguanine, including chemical modifications of 6-TG, so long as the structure of the 6-TG base is preserved. As used herein, the term "6-methyl-mercaptopurine" or "6-MMP" refers to 6-methyl-mercaptopurine or analogues thereof, including analogues having the same base structure, for example, 6-methyl-mercaptopurine ribonucleoside, 6-methyl-mercaptopurine ribonucleotide mono-, di-, and tri-phosphate, 6-methyl-mercaptopurine deoxyribonucleoside, and 6-methyl-mercaptopurine deoxyribonucleotide mono-, di- and tri-phosphate. The term "6-MMP" also includes derivatives of 6-methyl-mercaptopurine, including chemical modifications of 6-MMP, so long as the structure of the 6-MMP base is preserved.

6-MP drugs may be delivered as a suspension, solution, or emulsion in oily or aqueous vehicles, and may contain such formulary agents such as suspending, stabilizing and/or dispersing agents. Suitable aqueous vehicles include physiological saline, phosphate-buffered saline, and other vehicles for parenteral drug delivery, generically referred to as "intravenous solutions". Alternatively, the active ingredient may be in powder form, obtained by aseptic isolation of sterile solid or lyophilized from solution, with a suitable vehicle, e.g. sterile, pyrogen-free water, before use.

Methods of the Invention

Antigen specific immune tolerance is induced in a mammalian host by administering concurrently a toleragen and a T cell immunosuppressive agent, which may further be combined with administration of an antiproliferative agent, as described above. These agents may be formulated separately or together, usually separately. The agents are said to be administered concurrently when introduced into the host simultaneously in time or at different times during the course of a common treatment schedule. In the latter case, the compounds are administered sufficiently close in time to achieve the desired effect. Typically, if one agent is administered approximately within the in vivo half life of the other agent, the two agents are considered to be concurrently administered. Any active agent should be present in the patient at sufficient combined levels to be therapeutically effective.

The tolerization regimen is optionally preceded by a conditioning period, where during the conditioning period the suppressive agent or agents are administered in the absence of the toleragen for a period of from about 1 to 3 weeks. The period of time for conditioning will be sufficient to suppress T cell responses in the host prior to administration of the toleragen. The time period for conditioning may vary depending on the host, the suppressive agents, etc. The period of time may be empirically determined, or obtained from published sources.

The tolerization regimen requires that the T cell immunosuppressive agent be maintained for a period of time sufficient to induce immune tolerance. Usually the T cell immunosuppressive agent will be administered to the host for at least about 3 weeks, usually at least about 5 weeks, and may be at least about 8 weeks or more. The antiproliferative drug is also administered during this period of time, in a schedule appropriate to the drug, usually at least every other day, daily, twice daily or more. While the tolerization regimen can be continued for longer periods of time, it is usually desirable to minimize the period of time in which the patient is treated with the suppressive agents.

An important aspect of the invention is maintaining a high dose of the T cell immunosuppressive agent during the initial stages of the tolerization procedure. In pharmacokinetics, it is observed that the concentration of a drug in the bloodstream reaches a "peak" after administration, and then the blood levels drop to the lowest point, or "trough", before administration of the next dose. In the methods of the present invention, it is important to maintain therapeutic levels of the T cell immunosuppressive agent during this period of time, such that the "trough" levels do not drop to non-suppressive levels. This can be empirically determined by periodically measuring the concentration of the drug in the bloodstream to determine the trough values for a given administration protocol. The level of immunosuppression for a given concentration of drug can be determined empirically, as discussed previously, or obtained from published values. The concentration of the drug will be sufficient to prevent the in vivo initiation or maintenance of a T cell mediated immune response.

Increasing the trough levels to maintain suppressive levels of the drug can be accomplished by administering higher doses of the drug, or by administering a standard dose more frequently. For example, in humans, with cyclosporine A, it is desirable to have a trough blood level of not less than about 200 ng/ml, usually not less than about 300 ng/ml, and may be about 500 ng/ml or higher. Levels are known to induce tolerance in the canine species are about 400 ng/ml at the trough, however the appropriate level in other species will take into account the sensitivity of the host to the immunosuppressant being administered. In particular, humans may more sensitive to the effects of cyclosporine than canines. The dose ranges for humans may be lower than for canines due to the decreased rate of metabolism in general in humans relative to canines. It is expected that the human dose may be approximately one half of the canine dose (about 10 mg/kg/day to about 15 mg/kg/day) based on the differences in metabolic rates in order to achieve the same plasma levels or the same degree of physiologic effect. The levels required may be comparable to those used in de novo renal or other transplants (about 8+/−3 mg/kg/day) at which the trough level of about 350+/−150 ng/ml was achieved, Physicians Desk Reference, ed. 56 published by Medical Economics Co., Montvale, N.J., p 2381).

For example, the initial dose of the T cell immunosuppressive agent may be at a dose equivalent to at least about 125% of the standard dose for immunosuppression, at least about 150% of the standard dose, or 200% of the standard dose, or more. In other embodiments, the dose may be the conventional dose, administered more frequently, e.g. twice daily instead of daily, etc. A conventional dose for oral tacrolimus is 0.2 mg/kg/day. A conventional dose for sirolimus is 2 mg/kg/day. It will be appreciated by one of skill in the art that the standard dose will vary depending on the specific drug, on the method of administration, i.e. oral, intravenous, etc., and on the host.

At the end of the high dose period, the dose of the T cell immunosuppressive agent will be tapered off until the end of the tolerizing regimen, at which point it will be discontinued. Any convenient protocol may be used, for example by halving the dose every week or two weeks.

The high dose will be maintained for a period of time sufficient to allow the toleragen to be taken up by tolerizing cells, processed and presented on the cell surface, and for T cells to interact with such tolerizing cells, usually for at least about 2 weeks, more usually at least about 3 weeks, and may be for 4 weeks or more. The dose level and time interval can be determined to be sufficient by measuring the antibody titer using a method such as ELISA to assay the serum or plasma of the host at weeks 6 to 8 in the regimen. Hosts that are not tolerant will have mounted an immune response by near the end of the taper of the immune suppressive drugs. The period of time for which the high dose is necessary may include the conditioning period, such that if there is a two week conditioning period, then the high dose may be tapered off shortly after initiation of the tolerization regimen.

When an antiproliferative agent is included in the regimen, it will be administered at a conventional dose while the T cell immunosuppressive agent is administered, usually for at least about two weeks, more usually at least about 3 weeks, and may be for 4 weeks or more. For example, the standard dose of azathioprine is from about 1 to 5 mg/kg/day, where the upper end, from about 3 to 5 mg/kg/day is used initially, and the lower range, from about 1 to 3 mg/kg/day is given after establishment of the regimen. The anti-proliferative agent may also be given every other week. As described above for the T cell immunosuppressive agent, the period of time for which the initial dose is necessary may include the conditioning period, such that if there is a two week conditioning period, then the high dose may be tapered off shortly after initiation of the tolerization regimen. Usually it is preferable to taper off the dose, over the tolerizing regimen, by any convenient protocol.

The toleragen is administered at least 2 times, usually at least about 4 times, and may be administered 6 times or more, during the tolerization period. The toleragen will not be administered during the conditioning period, if there is one. In contrast to the suppressive agents, the toleragen will be administered less frequently, for example after about 4 days, about 7 days, about 10 days, and the like. Weekly administration is convenient.

The dose of toleragen will generally be lower than the therapeutic dose of the corresponding antigen, and may range from as much as the normal therapeutic dose of the antigen to as little as about 5% of the therapeutic dose, about 10% of the therapeutic dose, 50% of the therapeutic dose, and the like. Where the toleragen is a polypeptide it will be administered at a dose of at least about 0.005 mg/kg/week, usually at least about 0.01 mg/kg/week, more usually at least about 0.05 mg/kg/week; and usually not more than about 1 mg/kg/week. However, it will be appreciated that the specific dose will depend on the route of administration, activity of the agent, etc.

The dose of the toleragen is gradually raised to reach normal therapeutic doses starting after about 3 weeks, usually after about 4 weeks, and may be after about 6 weeks or 8 weeks. Where the toleragen and antigen are not identical, the patient may be switched to the antigen after the tolerization regimen, which change may involve administering a mixture of the two for a period of time.

The toleragen will be administered by any convenient route, usually intravenously, in a soluble form. More particularly, the toleragen can be formulated by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration.

In pharmaceutical dosage forms, the toleragen may be administered in the form of a pharmaceutically acceptable salts. They may also be used in appropriate association with other pharmaceutically active compounds. The following methods and excipients are merely exemplary and are in no way limiting. The toleragen can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Antigens suitable for the methods of the invention include a number of therapeutically active agents, particularly polypeptides, which may be immunologically active, growth factors, hormones, clotting factors, metabolic enzymes, etc. Examples of therapeutic proteins of interest include blood clotting factors, such as Factor VIII; alpha-glucosidase; iduronidase, therapeutic antibodies such as herceptin; DNAse; human growth factor; insulin; and the like.

Where the antigen of interest is an autoantigen, or where the host has been previously exposed to a therapeutic agent, it may be necessary to ablate some or all of the mature immune cells present in the patients. Such methods are known in the art, for example on may utilize a strong immunosuppressive agent, for example cyclophosphamide, antithymocyte globulin, total body irradiation (TBI), etc.

Autoantigens of interest for tolerization include the following. The toleragen may comprise one or a cocktail of autoantigens. For multiple sclerosis, proteolipid protein (PLP); myelin basic protein (MBP); myelin oligodendrocyte protein (MOG); cyclic nucleotide phosphodiesterase (CNPase); myelin-associated glycoprotein (MAG), and myelin-associated oligodendrocytic basic protein (MBOP); alpha-B-crystallin (a heat shock protein); OSP (oligodendrocyte specific-protein); citrulline-modified MBP (the C8 isoform of MBP in which 6 arginines have been de-imminated to citrulline), etc.

Autoantigens in rheumatoid arthritis include type II collagen; hnRNP; A2/RA33; Sa; filaggrin; keratin; citrulline; cartilage proteins including gp39; collagens type I, III, IV, V, IX, XI; HSP-65/60; IgM (rheumatoid factor); RNA polymerase; hnRNP-B1; hnRNP-D; cardiolipin; aldolase A; citrulline-modified filaggrin and fibrin.

Autoantigens in human insulin dependent diabetes mellitus include tyrosine phosphatase IA-2; IA-2β; glutamic acid decarboxylase (GAD) both the 65 kDa and 67 kDa forms; carboxypeptidase H; insulin; proinsulin; heat shock proteins (HSP); glima 38; islet cell antigen 69 KDa (ICA69); p52; two ganglioside antigens (GT3 and GM2-1); and an islet cell glucose transporter (GLUT 2).

Autoantigens for myasthenia gravis may include epitopes within the acetylcholine receptor. Autoantigens targeted in pemphigus vulgaris may include desmoglein-3. Sjogren's syndrome antigens may include SSA (Ro); SSB (La); and fodrin. The dominant autoantigen for pemphigus vulgaris may include desmoglein-3.

Immune rejection of tissue transplants, including lung, heart, liver, kidney, pancreas, and other organs and tissues, is mediated by immune responses in the transplant recipient directed against the transplanted organ. Allogeneic transplanted organs contain proteins with variations in their amino acid sequences when compared to the amino acid sequences of the transplant recipient. Because the amino acid sequences of the transplanted organ differ from those of the transplant recipient they frequently elicit an immune response in the recipient against the transplanted organ. Rejection of transplanted organs is a major complication and limitation of tissue transplant, and can cause failure of the transplanted organ in the recipient. The chronic inflammation that results from rejection frequently leads to dysfunction in the transplanted organ.

The toleragen for an intended transplant recipient may include one or more major histocompatibility antigens, e.g. HLA-A, HLA-B, HLA-C, HLA-DR, HLA-DQ, HLA-DP, etc., and may comprise a cocktail of such antigens, where the antigens will include those not matched between the recipient and the donor. As these are cell surface proteins, the administered form may be a soluble form, i.e. one that is truncated at the transmembrane domain.

While not required, in order to enhance tolerance after cessation of the suppressive agents, a maintenance dose of the toleragen may be provided, where the maintenance dose is provided at a dose equivalent to 0.056 mg/kg per week or lower in dose, or of 1/10 that dose or lower, or less frequent as in once per month or once every few months or less, or both dose and frequency. In cases where the toleragen is different from the antigen, the toleragen will be used for the maintenance phase, if a maintenance phase is required.

The agents utilized in the methods of the invention may be provided in a kit, which kit may further include instructions for use. Such a kit will comprise a toleragen, usually in a dose and form suitable for administration to the host. The kit may further comprise a T cell immunosuppressive agent, in a form suitable for administration, and may further include assay reagents for monitoring blood levels of the agent, and/or for determination of suppression of T cell activity. An anti-proliferative agent may also be included, in a form suitable for administration.

A kit may also provided for the conjugation of an antigen, particularly a polypeptide antigen, to a high uptake moiety, in order to generate a toleragenic composition. For example, a moiety such as a mannose 6 phosphate group, either conjugated to a linker suitable for linking sugars and polypeptides, as described above, may be provided. The high uptake moiety may also be provided in an unconjugated form, in combination with a suitable linker, and instructions for use.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Experimental

Example 1

Induction of Tolerance to Human α-L-iduronidase in Normal and MPS I Dogs

Mucopolysaccharidosis I is a genetic condition caused by mutations in the alpha-L-iduronidase gene leading to a deficiency in the enzyme iduronidase. This deficiency leads to a progressive multi-system lysosomal storage disorder that includes coarsened facial features, large tongue, large liver and spleen, respiratory problems, heart problems, joint stiffness and bone disease. The disease leads to death in patients usually in their first or second decade of life.

The deficient enzyme iduronidase is a lysosomal hydrolase that cleaves the terminal iduronide residue of heparan and dermatan sulfate. The enzyme can be made in recombinant cells and is produced with a mannose 6-phosphate marker on post-translationally attached carbohydrates, which is important for its uptake into cells. Enzyme replacement therapy has been proposed as a method of treatment, in which a recombinant form of the enzyme is administered intravenously, distributes to tissues and is taken up into cells via the mannose 6-phosphate receptor. The therapy has been studied in dogs and most recently in humans (Kakkis et al. (2001) *NEJM* 344:182).

The administration of recombinant human α-L-iduronidase to normal or MPS I dogs induces a strong immune response to the enzyme (Shull et al. (1994) *P.N.A.S.* 91:12937-12941, Kakkis et al. (1996) *Biochem Mol. Med.* 58:156-167) which mimics that observed in human MPS I patients. These responses may interfere with the efficacy of enzyme therapy. To study methods to induce tolerance, normal dogs were administered the heterologous human α-L-iduronidase protein under various conditions designed to prevent an active immune response and to allow the induction of tolerance. The studies demonstrate that the appropriate dose of cyclosporine and azathioprine, followed by the weekly administration of the recombinant human α-L-iduronidase and the gradual removal of the immunosuppressive drugs can induce tolerance to the enzyme that lasted at least 6 months of weekly enzyme administration. A less frequent dose of cyclosporine, with or without the addition of the addition of intrathymic injection or anti-T cell monoclonal antibodies have no impact on tolerance induction. CsA alone at the right dose without Aza, did not induce tolerance.

The tolerance regimen utilized CsA+Aza treatment (with CsA dose at 25 mg/kg/day), along with toleragen infusions on the schedule shown in FIG. 1. Additional treatments indicated, such as intrathymic injection and monoclonal antibodies, are shown as examples of treatments that did not work or did not enhance tolerance induction. These non-effective regimens are included in the examples to provide contrast with the response of those canines optimally tolerized to the antigen by the invention.

For non-tolerance inducing regimens using intrathymic injection or monoclonal antibodies but not the 25 mg/kg/day dose of CsA, day 4 is the day the canines receive intrathymic injection. In the bottom regimen diagram (FIG. 1) for IT+drugs, the canine receives CsA+Aza for 0-4 days, and then receives an intrathymic injection (IT Inj. or ITI). If monoclonal antibodies are indicated, they are given in the days prior to IT injection. The exact dosing performed depends on the experiment. In non-tolerant experiments, the canines received every other day CsA at 25 mg/kg on alternate days with the Aza. In tolerizing experiments, the canines received daily CsA with alternate day Aza. In either case, the dose administered was halved in the sequence described. For canines receiving the tolerizing regimen, the top regimen diagram describes the course of treatment. The canine PA received CsA only, beginning 4 days before infusions begin and tapering following the upper tolerance inducing regimen.

Materials and Methods

Animals. Normal and MPS I canines were obtained from the MPS I canine colony at Harbor-UCLA. The dogs are a cross between beagles and Plott hounds and average 12-20 kg in weight. The canines were under 2 years of age and at least 4 months of age for these experiments.

Canines BI, BE, BC, BO, JA, JO, ME, MA, MO, and PA were normal or carrier canines from the MPS I canine colony and therefore are unaffected with MPS I, and received a series of different regimens that did not induce tolerance. When CsA+Aza were part of the regimen, they received the CsA every other day. BI received phosphate buffered saline intrathymic injection (ITI); BE and BC received iduronidase ITI; BO received CsA(qod)+Aza+ITI; JA, JO, ME, MA, and MO received CsA+Aza, ITI and various monoclonal antibodies that deplete mature T cells. PA received daily CsA dose but unlike dogs that became tolerant, she did not receive Aza.

Canines RH, RI, and RO were normal or carrier canines from the MPS I colony that received at minimum the CsA+Aza regimen that induces tolerance and in the case of RH and RI, they also received intrathymic injection. The CsA was administered daily.

Canine RU is an MPS I affected dog that received no tolerance regimen and served as a control. Canines PE, SA, and NI are MPS I affected dogs that received the tolerance inducing regimen of CsA+Aza.

Monoclonal antibodies. A series of monoclonal antibodies were obtained from Peter Moore (UC Davis Veterinary School) and were specific to canine T cell receptor (anti-TCR), canine CD3 antigen (anti-CD3; IgG2b)) and the canine equivalent of Thy-1 (anti-Thy1; IgG1). The anti-TCR antibody was prepared by growing the hybridoma in low serum containing medium and purification of the antibody by protein A chromatography. The anti-CD3 and anti-Thy1 antibodies were prepared by production of ascites in mice using the hybridomas, CA17.6B3 and CA 1.4G8 and protein A purification, at a contract laboratory (Strategic Biosolutions). When utilized, the monoclonal antibodies were administered in 2 or 3 doses just prior to ITI.

Immunosuppressive drugs. Cyclosporine (Neoral or Sandimmune) and Azathioprine (Imuran) were obtained from a local pharmacy. Both drugs were dosed orally at the dose and frequency noted in the experiments. The two regimens tested are shown immediately below.

Immunosuppressive Drug Regimen with Daily CsA Dosing that induces tolerance:
  CsA Neoral® 25 mg/kg/day divided bid po
  Aza Imuran® 5 mg/kg qod po
  CsA+Aza given at full dose from day 0-32, ½ dose from day 33-46, and ¼ the dose from 47-60, and then terminated.
  Animals monitored for adverse reactions
  CsA peak and trough levels are monitored and dose adjusted to maintain a target trough level of 400-500 ng/ml in the circulation.

Immunosuppressive Drug Regimen with Every Other Day CsA dosing that does not induce tolerance:
  CsA Neoral® 25 mg/kg/every other day divided bid po
  Aza Imuran® 5 mg/kg every other day on alternate days from CsA
  CsA+Aza given at full dose from day 0-18, ½ dose from day 19-32, and ¼ dose from 33-46 and $\frac{1}{8}^{th}$ from day 47-60, and then terminated Animals monitored for adverse reactions
  CsA peak and trough levels monitored and a trough level of 100-200 ng/ml in the circulation.

Intrathymic injection. During general anesthesia a 3-inch incision was made in the left-side at the $3^{rd}$ intercostal space. The incision was continued through all muscle layers until the chest cavity is reached. A rib separator was employed and the thymus observed directly as a vascularized, lobed organ beneath the lungs. The enzyme solution was injected into the thymus with a syringe and 25 G needle. A "zig-zag" pattern was made when inserting the needle into the thymus in an attempt to prevent enzyme leakage upon withdrawal of the needle. The thymus was visually inspected for any leakage of enzyme solution made visible by Evan's Blue dye. The surgery site was closed and respiratory function restored using vacuum drawn through a Foley catheter inserted in the chest cavity. Antibiotics were applied to all incision sites and surgery was followed by a short course of antibiotics and pain management medication as necessary.

Injection solution, 1.5 mL total: 1 mg/kg of 12.1 mg/mL iduronidase ($3 \times 10^6$ U/mL). Bring to 1.5 mL with 40% PEG+2 mg/mL Evan's Blue dye in acidic PBS (Final solution approximately 6% PEG, 0.3 mg/mL Evan's).

Enzyme Infusions. Recombinant iduronidase is prepared in a highly purified form and has been demonstrated to have high uptake potential with half maximal uptake into Hurler fibroblasts at an enzyme concentration of about 1 nanomolar ($K_{uptake}$) and a uptake specification less than 3.3 nanomolar. For toleragenic infusions, 14,000 U/kg/week α-L-iduronidase in 50 mL infusion in saline with 1 mg/mL canine albumin, and 10 mM NaPO4 was administered intravenously over 2 hours ($1^{st}$ hour 3,000 U/kg/hr; $2^{nd}$ hour 11,000 U/kg/hr). Animals monitored for an anaphylactic reaction. 250,000 U is equal to 1 mg of protein.

Results

The basic outline of the experimental plan is shown in FIG. 1. The entire cohort of dogs were pretreated with immunosuppressive drugs, followed by an IT injection if scheduled, and then beginning 2 weeks later, a series of weekly challenges of iduronidase. The canines received either the non-tolerance inducing regimen with every other day CsA (see regimens above) with or without other treatments (intrathymic injection, monoclonal antibodies), or the tolerance inducing regimen with daily CsA dosing with or without the other treatments. One dog, PA received the daily CsA dose but no Aza.

Canines were initiated on immunosuppressive drugs at day 0, equivalent to 18 days prior to the first enzyme challenge. If scheduled, the canines received monoclonal antibodies by intravenous infusion (2-5 mg) just prior to ITI. On day 4, the dogs received, if scheduled, an intrathymic injection of iduronidase at 1 mg/kg. Two weeks later, the dogs were begun on a weekly schedule of iduronidase enzyme infusions consisting of a weekly intravenous infusion of 14,000 U/kg (0.056 mg/kg/wk) of human recombinant iduronidase. The dose of CsA and Aza were halved every two weeks as noted in the materials and methods as indicated.

After 6-8 weeks of enzyme challenges, canines receiving the optimum protocol of CsA (daily)+Aza with or without IT injection (FIG. 2 open symbols), were tolerant to iduronidase whereas dogs receiving other regimens had strong immune responses as assessed by ELISA (FIG. 2 closed symbols). The iduronidase tolerant canine RO was continued on weekly enzyme challenges for 6 months without induction of a significant ELISA titer to iduronidase.

The antibody titer to iduronidase in the non-tolerant and tolerant canines is shown in Table 1. Only canines that completed at least 12 weeks are included in the table; non-tolerant canines BE, BI, BC and BO were stopped at 7 weeks with titers already of 21-74 OD/µl serum. The non-tolerant canines had induction of 181 fold from a baseline level of 0.8 to a mean induction level of 144.6 ELISA OD units per microliter of serum. The tolerant dogs had a titer increase of 13 fold, from an initial 0.4 at baseline to 5.2 after treatment with iduronidase. The non-tolerant dogs had a ~28 fold higher induction of antibodies to iduronidase than the tolerant dogs. One dog NI had the highest titer in the tolerant group of 13.8. This dog vomited the CsA dose on multiple occasions which may account for the less complete induction of tolerance, and further supports the critical nature of the CsA dosing. PA received the preferred daily dosing of CsA but did not receive Aza and did not tolerize. Though two of the tolerant normal dogs, RH and RI, also received intrathymic injection, the injection was not necessary as tolerance in canine RO showed.

TABLE 1

Immune response in tolerant and non-tolerant canines

| | Canine | Treatment | Antibody Titer to Iduronidase (OD Units/µL undiluted serum) | | | |
|---|---|---|---|---|---|---|
| | | | Pre-treatment | Mean | Post-treatment | Mean |
| Non-Tolerant (every other day CsA plus other | JA | (CsA + Aza + ITI + TCR mAb) | 0 | 0.8 | 230.7 | 144.6 |
| | JO | (CsA + Aza + ITI + TCR mAb) | 2.6 | | 101.2 | |
| | ME | (CsA + Aza + ITI + TCR mAb) | 0.3 | | 60.2 | |

TABLE 1-continued

Immune response in tolerant and non-tolerant canines

Antibody Titer to Iduronidase (OD Units/μL undiluted serum)

| | Canine | Treatment | Pre-treatment | Mean | Post-treatment | Mean |
|---|---|---|---|---|---|---|
| treatments) | MA | (CsA + Aza + ITI + CD3/Thy1/TCR mAb) | 1.5 | | 120.8 | |
| | MO | (CsA + Aza + ITI + CD3/Thy1/TCR mAb) | 0 | | 377.9 | |
| | PA | CSA) | 0.3 | | 64.4 | |
| | RU | (No Drug Contol MPS I Affected) | 1.2 | | 56.7 | |
| | RH | (CSA(daily) + Aza + ITI) | 0.3 | 0.4 | 8.7 | 5.2 |
| | RI | (CSA(daily) + Aza + ITI) | 0.3 | | 0.5 | |
| | RO | (CSA(daily) + Aza) | 0.2 | | 0.7 | |
| | PE | (CSA(daily) + Aza + MPS I Affected) | 0.6 | | 0.8 | |
| | SA | (CSA(daily) + Aza + MPS I Affected) | 0.4 | | 6.8 | |
| | NI | (CSA(daily) + Aza + MPS I Affected) | 0.8 | | 13.8 | |

In table 1, the antibody titer to iduronidase for 6 tolerant canines and 7 non-tolerant canines is shown as OD Units/μL undiluted serum as measured by ELISA. The canines received drug or other treatments as described in example 1, and were administered iduronidase. All canines received 0.056 mg/kg/week rh iduronidase intravenous challenges. Pre treatment ELISA values represent serum antibody levels prior to first antigen challenge with iduronidase. Post treatment points represent serum antibody levels at week 12 of enzyme challenge, or at latest point measured (ME, MA, MO at week 11; PA at week 9). The mean post treatment antibody titers for tolerant canines (5.2 OD/microliter) is $\frac{1}{25}^{th}$ the titer of non-tolerant canines (144.6 OD/microliter).

The greatly reduced response to iduronidase in the tolerant dogs occurs despite the fact that the dogs were off all immunosuppressive drugs by the end of week 6. The titer in the tolerance dogs stayed low for several months and was studied in RO and SA for 6 months of weekly infusions (FIG. 2). Attempts to induce tolerance to another antigen ovalbumin with mannose terminated N-linked oligosaccharides, did not succeed. This data suggests that the higher uptake and broadly present mannose 6-phosphate receptor may be required or that mannose receptor mediated uptake is not sufficient for the toleragen to successfully induce tolerance.

Induction of tolerance to a therapeutic protein has been achieved in canines. Canines treated with an optimal regimen of CsA and Aza, showed a dramatically reduced immune response to weekly infusions of the iduronidase enzyme that lasted at least 4-6 months. The tolerance does not depend on other reagents or procedures such as monoclonal antibodies or intrathymic injection. The tolerant state is maintained in the absence of immunosuppressive drugs for at least 6 months.

The key difference between the tolerant dogs and the other dogs was the use of CsA daily. CsA alone, however, was not sufficient in dogs, as canine PA did not tolerize using daily CsA alone. The immunosuppressive drugs alone cannot induce tolerance in dogs, and the use of antigen infusions under the protective cover of immunosuppressive drugs is a key part of the tolerance protocol. The enzyme is likely being presented as a tolerizing antigen while the T cells that might be activated are held back by the drugs.

Other parts of the regimen were intended to improve the chances of inducing tolerance but had no effect. Intrathymic injection was designed to present antigen in a site known to be tolerogenic, but this had no effect and if anything, led to earlier immune response. It appears that such peripheral presentation and tolerization in this model is more effective.

Monoclonal antibodies to T cell markers also did not contribute to tolerance. These monoclonals were intended to deplete as much as 90% of mature T cells from the circulation as has been shown in pilot experiments, but their use did not add, and was not required for, tolerance.

While the host canine might have been an important factor, in fact, tolerance to human iduronidase was induced in normal canines with endogenous iduronidase as well as in MPS I affected canines with no endogenous iduronidase.

Example 2

Induction of Tolerance to Therapeutic Iduronidase in MPS I Affected Dogs and Maintenance of Tolerance During High Therapeutic Dose Infusions Induction of tolerance must prevent a clinically significant immune response to the therapeutic protein to be useful in the clinic. MPS I canines on enzyme replacement therapy with iduronidase respond with high-titer antibodies that delay clearance or alter the stability of the enzyme, prevent uptake of the enzyme and likely limit the efficacy of the enzyme therapy. The same phenomenon has been reported in other animal models.

To study whether naïve MPS I canines can be tolerized to iduronidase and subsequently receive high dose therapeutic levels of enzyme on a weekly basis, a series of four MPS I affected dogs were tolerized (3 dogs) or kept as control (1 dog). After 12 weeks, the tolerant canines received an increasing weekly dose of iduronidase and finally received at least 6 weeks of therapeutic doses of enzyme, without a significant immune response. The non-tolerant control dog had a rapidly rising titer to the enzyme as has been observed previously and infusions were terminated at week 16 due to an anaphylactic reaction.

Methods and Materials

Animals. MPS I dogs were obtained from the MPS I canine colony at Harbor-UCLA. The dogs are a cross between beagles and Plott hounds and average 12-20 kg in weight. The canines were under 2 years of age and at least 4 months of age for these experiments.

Immunosuppressive drugs. Cyclosporine (Neoral or Sandimmune) and Azathioprine (Imuran) were obtained from a local pharmacy. Both drugs were dosed orally at the dose and frequency noted in the experiments. The regimen tested is shown immediately below.

Immunosuppressive Drug Regimen with Daily CsA Dosing that induces tolerance: This regimen was as described in Example 1.

Enzyme Infusions. Recombinant iduronidase is prepared in a highly purified form and has been demonstrated to have high uptake potential with half maximal uptake into Hurler fibroblasts at an enzyme concentration of about 1 nanomolar ($K_{uptake}$) and a uptake specification less than 3.3 nanomolar. Canines were administered 14,000 U/kg/week α-L-iduronidase or higher dose as dose was ramped up, in a 50 mL infusion in saline containing 1 mg/mL canine albumin, 10 mM $NaPO_4$, pH 5.8. Administered intravenously over 2 hours ($1^{st}$ hour 3,000 U/kg/hr; $2^{nd}$ hour 11,000 U/kg/hr, or a higher rate in the $2^{nd}$ hour depending on the dose). Animals were monitored for anaphylactic reaction.

Results

Tolerance induction in three MPS I dogs but not a control MPS I dog Three MPS I dogs were tolerized using the tolerance regimen including 18 days of CsA+Aza prior to initiating weekly enzyme infusions. One MPS I dog served as a control and did not receive the tolerance regimen. The 4 canines received 0.056 mg/kg/week intravenous iduronidase infusions at weeks 1-12. The antibody titer to iduronidase in the three tolerant MPS I dogs (FIG. 3; open symbols) and one non-tolerant MPS I dog (FIG. 3; closed symbol) are shown as measured by ELISA. Low antibody levels (<20 OD) with continued antigen challenge indicate tolerance. The tolerizing drug regimen (CsA+Aza) ends at week 7 of enzyme challenge and low antibody levels beyond that point are indicative of induced tolerance.

Tolerant MPS I dogs are tolerant to full therapeutic dose enzyme therapy The four MPS I canines received a stepwise increase in iduronidase dose over 3 weeks to therapeutic doses of 0.500 mg/kg/week at week 15 of enzyme challenge. This is the same dose used in prior therapeutic trials in the MPS I dogs and is used in human MPS I enzyme therapy (Kakkis et al 2001, supra.) Antibody levels in tolerant canines remained <20 OD Units at week 15 compared to control RU antibody levels of >500 OD Units at week 15 in response to increasing antigen dose. Two MPS I canines previously treated with this dose of enzyme (0.5 mg/kg/wk) had titers of 1800 and 2000 by week 14 of enzyme therapy for comparison.

At week 16, non-tolerant canine RU had a serious clinical anaphalactoid reaction during the infusion and treatment was ended. The tolerant canines did not exhibit anaphalactoid reactions during the infusions.

MPS I dogs completely deficient in the antigen iduronidase, canine or human, can be tolerized to the human iduronidase protein reproducibly. These tolerant dogs can also receive full therapeutic doses of enzyme without a significant immune response. This result indicates that the tolerance induced is robust and can protect a dog from higher levels of exposure to an antigen including levels that might be expected during therapeutic protein administration.

Example 3

Induction of Tolerance to Alpha Glucosidase

Induction of tolerance to iduronidase infusions has been demonstrated in normal and MPS I dogs using a regimen of daily CsA+Aza, followed by weekly infusions of tolerizing antigen while tapering the immunosuppressive drugs. To demonstrate that tolerance can be induced to another enzyme with high affinity uptake characteristics, recombinant human alpha glucosidase was prepared and studied with the tolerance regimen. Two normal canines were studied, one with the tolerance regimen and one control. Weekly infusions with glucosidase began and by week 3, the control dog had a rising immune titer. By week 5, the control dog a 100 fold higher titer, and the treated dog had no significant titer. The data shows that the tolerance regimen can be successfully used with other antigens.

Materials and Methods

Animals. MPS I dogs were obtained from the MPS I canine colony at Harbor-UCLA. The dogs are a cross between beagles and Plott hounds and average 12-20 kg in weight. The canines were under 1 year of age and at least 4 months of age for these experiments.

Immunosuppressive drugs. Cyclosporine (Neoral or Sandimmune) and Azathioprine (Imuran) were obtained from a local pharmacy. Both drugs were dosed orally at the dose and frequency noted in the experiments. The regimen tested is shown immediately below.

Immunosuppressive Drug Regimen with Daily CsA Dosing that induces tolerance:
CsA Neoral® 25 mg/kg/day divided bid po
Aza Imuran® 5 mg/kg qod po
Doses halved for all drugs each 2 weeks after first enzyme infusion
Animals monitored for adverse reactions
CsA peak and trough levels were monitored to maintain an optimal target trough level of 400-500 ng/ml in the circulation.

Enzyme Infusions. Recombinant alpha-glucosidase is prepared in a highly purified form and has been demonstrated to have high uptake potential with half maximal uptake into fibroblasts at an enzyme concentration of about 1 nanomolar ($K_{uptake}$) and a uptake specification less than 3.3 nanomolar. Infusions were performed with 0.056 mg/kg/week recombinant human alpha glucosidase in a 50 mL infusion of saline and 10 mM $NaPO_4$, pH 5.8. The infusions were administered intravenously over 2 hours ($1^{st}$ hour 21% of the total dose; $2^{nd}$ hour the balance of the enzyme). Animals were monitored for anaphylactic reaction.

Results

Control canine ST received no drug treatment and began receiving alpha-glucosidase by weekly intravenous infusions. By 3 weeks, a significant titer was detected and the titer increased to more than 100 OD units per microliter of serum by week 4. Subsequently, the titer ranged between almost 100-200 units per microliter of serum. In contrast, canine SC received the CsA+Aza regimen and had minimal if any immune response during 12 weeks of infusions. This includes weeks 7-12 in which no immunosuppressive drugs were administered.

The regimen of CsA+Aza with infusions of tolerizing antigen on a weekly basis can induce tolerance to other antigens. The result demonstrates the broader utility of the regimen and tolerizing antigen protocol in inducing a profound state of immune tolerance. In particular, immune response to alpha-glucosidase has been reported to inhibit or limit the utility of enzyme replacement therapy in Pompe patients. This result demonstrates the utility of the tolerance regimen in preventing an immune response to this therapeutic protein.

Example 4

Induction of Tolerance is Dependent on CSA Dose

Early work on developing a tolerance protocol focused on a combination of intrathymic injection, immunosuppressive drugs and mature T cell-depleting monoclonal antibodies. It was thought that a complete combination of tolerizing antigen expression (intrathymic injection), suppression of mature antigen-specific T cell responses (CsA and Aza) as well as depletion of mature T cells capable of responding to antigen, was necessary to block an activating immune response and prepare the immune system to accept the antigen exposure. During the development of this work, a canine JH, became tolerant though the canine received only ITI and CsA+Aza. Further analysis of this canine demonstrated that his metabolism of CsA led to substantially higher serum levels of CsA. This finding became the core result that allowed further experiments into the induction of tolerance with the immunosuppressive drugs and toleragen only.

Materials and Methods

Animals. Normal and MPS I canines were obtained from the MPS I canine colony at Harbor-UCLA. The dogs are a cross between beagles and Plott hounds and average 12-20 kg in weight. The canines were under 2 years of age and at least 4 months of age for these experiments.

Monoclonal antibodies. A series of monoclonal antibodies were obtained from Peter Moore (UC Davis Veterinary School) and were specific to canine T cell receptor (anti-TCR), canine CD3 antigen (anti-CD3; IgG2b)) and the canine equivalent of Thy-1 (anti-Thy1; IgG1). The anti-TCR antibody was prepared by growing the hybridoma in low serum containing medium and purification of the antibody by protein A chromatography. The anti-CD3 and anti-Thy1 antibodies were prepared by production of ascites in mice using the hybridomas, CA17.6B3 and CA1.4G8 and protein A purification, at a contract laboratory (Strategic Biosolutions). When utilized, the monoclonal antibodies were administered in 2 or 3 doses just prior to ITI.

Immunosuppressive drugs. Cyclosporine (Neoral or Sandimmune) and Azathioprine (imuran) were obtained from a local pharmacy. Both drugs were dosed orally at the dose and frequency noted in the experiments. The use of Neoral or Sandimmune was evaluated as a factor in whether tolerance was induced and was not found to be factor.

Immunosuppressive Drug Regimen with Every Other Day CsA dosing that does not induce tolerance:

CsA Neoral® 25 mg/kg/every other day divided bid po
    Aza Imuran® 5 mg/kg every other day on alternate days from CsA
    CsA+Aza given at full dose from day 0-18, ½ dose from day 19-32, and ¼ th dose from 33-46 and $\frac{1}{8}^{th}$ from day 47-60, and then terminated
    Animals monitored for adverse reactions
    CsA peak and trough levels monitored and a trough level of 100-200 ng/ml in the circulation.

Intrathymic injection. During general anesthesia a 3-inch incision was made in the left-side at the $3^{rd}$ intercostal space. The incision was continued through all muscle layers until the chest cavity is reached. A rib separator was employed and the thymus observed directly as a vascularized, lobed organ beneath the lungs. The enzyme solution was injected into the thymus with a syringe and 25 G needle. A "zig-zag" pattern was made when inserting the needle into the thymus in an attempt to prevent enzyme leakage upon withdrawal of the needle. The thymus was visually inspected for any leakage of enzyme solution made visible by Evan's Blue dye. The surgery site was closed and respiratory function restored using vacuum drawn through a Foley catheter inserted in the chest cavity. Antibiotics were applied to all incision sites and surgery was followed by a short course of antibiotics and pain management medication as necessary.

Injection solution: 1.5 mL total; 1 mg/kg of 12.1 mg/mL iduronidase ($3\times10^6$ U/mL). Bring to 1.5 mL with 40% PEG+2 mg/mL Evan's Blue dye in acidic PBS (Final solution approximately 6% PEG, 0.3 mg/mL Evan's). Enzyme injection: 14,000 U/kg/week α-L-iduronidase in 50 mL infusion in saline with 1 mg/mL canine albumin, and 10 mM $NaPO_4$ administered intravenously over 2 hours ($1^{st}$ hour 3,000 U/kg/hr; $2^{nd}$ hour 11,000 U/kg/hr). Animals were monitored for anaphylactic reaction.

Results

Early tolerance experiments included CsA dosing at an every other day interval. These early experiments sought to establish whether ITI, immunosuppressive drugs and/or monoclonal antibodies that deplete T cells are required for tolerance induction. FIG. 5 shows the results for some early canines studied using ITI and drugs.

BI is a control dog that received an ITI of PBS only, and BE and BC were two dogs treated with ITI of iduronidase. None of the three were tolerant as titers exceeded 20 by 7 weeks. BO received every other day CsA+Aza in addition to ITI and he also was not tolerant with a titer of 42 by 7 weeks. JA and JO had the same regimen but in addition, an anti-TCR monoclonal antibody was infused prior to the ITI to determine if depleting T cells might allow the induction of tolerance. Both canines mounted immune responses and reached titers of 148 and 135 by 12 weeks. Curiously, the control dog JH did not mount an immune response even though he had the CsA+Aza and ITI protocol that had previously not worked with BO. The tolerance included a period of modest titer to iduronidase reaching a peak of 15.1 at week 1 and later declining to 7.1 at week 18.

Evaluation of the routine CsA levels showed a pattern that explains this result. Most dogs with every other day CsA had trough levels of 60-190 ng/ml though one dog (JO) reached 342 (Table 2). None of these dogs were tolerant. JH had a level of 570 which exceeded the other dogs by at least 200 ng/ml. The dog received the correct regimen based on a review of cage and drug administration records and yet the level was much higher.

JH was tolerized to iduronidase infusions using a regimen of CsA+Aza and ITI. Curiously, he had a much higher level of Csa in his serum which suggested that the level of CsA might be a critical factor. Following this experiment, further work on CsA dosing demonstrated that daily CsA dosing could maintain the trough levels above 400 ng/ml and that this, with every other day Aza dosing, was sufficient to induce tolerance.

TABLE 2

Comparison of Cyclosporine trough blood levels in iduronidase non-tolerant and iduronidase tolerant canines

| | Canine | Treatment | Trough CsA Level (ng/mL) | Mean |
|---|---|---|---|---|
| Non-Tolerant | BO | (CsA + Aza + ITI) | 190 | 148 |

TABLE 2-continued

Comparison of Cyclosporine trough blood levels in iduronidase non-tolerant and iduronidase tolerant canines

| | Canine | Treatment | Trough CsA Level (ng/mL) | Mean |
|---|---|---|---|---|
| (every other day CsA | JA | (CsA + Aza + ITI + TCR mAb) | 63 | |
| plus other treatments) | ME | (CsA + Aza + ITI + TCR mAb) | 60 | |
| | MA | (CsA + Aza + ITI + CD3/Thy1/TCR mAb) | 120 | |
| | MO | (CsA + Aza + ITI + CD3/Thy1/TCR mAb) | 110 | |
| Tolerant | JH | (CsA + Aza + ITI) | 570 | |
| (every other day CsA plus other treatments) | | | | |
| Tolerant | RH | (CsA(daily) + Aza + ITI) | 520 | 545 |
| (Tolerance drug regimen: | RI | (CsA(daily) + Aza + ITI) | 450 | |
| daily CsA plus Aza) | RO | (CsA(daily) + Aza) | 680 | |
| | PE | (CsA(daily) + Aza, MPS I Affected) | 440 | |
| | SA | (CsA(daily) + Aza, MPS I Affected) | 520 | |
| | NI | (CsA(daily) + Aza, MPS I Affected) | 660 | |
| Non-Tolerant (daily CsA, no Aza) | PA | (CsA(daily) only) | 490 | |

In table 2, the cyclosporine trough blood levels for tolerant and non-tolerant canines are shown as ng/mL blood. Cyclosporine levels were measured after at least 4 consecutive doses of cyclosporine. PA received daily cyclosporine treatment alone beginning 4 days before initial iduronidase challenge and was not tolerized to iduronidase. All other canines received immunosuppressive drugs beginning 18 days before first intravenous iduronidase challenge (4 days before ITI). All canines received 0.056 mg/kg/week rh iduronidase intravenous challenges. Successful tolerance to iduronidase was consistently associated with cyclosporine trough levels of 400-700 ng/mL. Canines with cyclosporine trough levels less than 400 ng/mL were not tolerized to iduronidase. (CsA=Cyclosporin A; Aza=Azathioprine; ITI=Intrathymic injection of iduronidase; mAb=Monoclonal antibody).

Table 2 shows additional data from other tolerized dogs corroborating the role of CsA dose in the tolerizing regimen. The non-tolerant dogs on the top section of the table received every other day CsA at 25 mg/kg and the 6 dogs treated with drugs with or without other treatments had trough CsA levels of 60-190 ng/ml, with one case JO at 342 ng/ml. These levels are taken after at least 4 doses of the drugs had been given during the regimen. The mean CsA level of the non-tolerant dogs is 148 ng/ml. In the third section, the tolerant dogs had trough CsA levels of 440-680 and a mean of 545 ng/ml, more than 3 fold higher. JH had level shown in the second section of the table of 570 ng/ml and though his dosing was only every other day, the level was high enough and he became tolerant. In contrast, PA shown in the fourth section of the table had an adequate CsA level of 490, but did not have Aza as well, and did not become tolerant. These data demonstrate the importance of an adequate CsA effect in the tolerance protocol.

Example 5

Induction of Tolerance is Long-Lasting without Chronic Toleragen Stimulation

The induction of tolerance by a toleragen is particularly useful if the tolerant state is long-lasting, even in the absence of toleragen administration. To address the stability of the tolerant state, canines that were tolerant and non-tolerant were retained for varying intervals of time and then rechallenged with iduronidase infusions. The data show that for at least 6 months, a tolerant animal remains tolerant to iduronidase infusion even without continuous toleragen or antigen exposure.

Methods and Materials

Tolerance was induced as described in the above examples for each canine noted (the same initials are used). JO was the canine tolerized with CsA dosing at every other day, unlike the other canines. This canine did not have complete tolerance initially but a muted antibody response. Other tolerance canines were fully tolerant based on studies described in other examples. Iduronidase was the same high uptake iduronidase as described above. The canines were challenged with 0.58 mg/kg of enzyme administered intravenously on a weekly basis for 3-6 doses.

Results and Discussion

In FIG. 6, the titers of canines that were tolerant or non-tolerant are shown with a gap indicated for the period in which no toleragen or therapeutic infusions occurred. As little as 5 weeks and as much as 6 months of toleragen hiatus did not change the response of the tolerant dogs, who remained tolerant and did not mount a significant immune response. The non-tolerant dog RU showed a >20 fold induction in antibody titer after receiving 2 doses of enzyme after a 4.5 month hiatus. The dog JH showed some response at 3 weeks of reinduction that exceeded that of most tolerant dogs but did not reach that of a sensitized non-tolerant dog RU. JH also had a more significant response when originally challenged and was not as tolerant as the dogs tolerized with the optimal regimen. His original titer pattern also plateaued and declined with continued infusions, which will be studied in this case.

These data demonstrate that tolerance induced by the methods and compositions of the present invention are long lasting and clinically useful.

Example 6

Induction of Tolerance in Humans

Materials and Methods

Patients. Patients with mucopolysaccharidosis I are selected for treatment. The patients are evaluated at base line and at 6, 12, 26, and 52 weeks by detailed clinical examinations, magnetic resonance imaging of the abdomen and brain, echocardiography, range-of-motion measurements, polysomnography, clinical laboratory evaluations, measurements of leukocyte α-L-iduronidase activity, and urinary glycosaminoglycan excretion.

Immunosuppressive drugs. Cyclosporine (Neoral or Sandimmune) and Azathioprine (Imuran) are obtained from commercial sources. Both drugs are dosed orally at the dose and frequency as follows: CsA Neoral® 12.5 mg/kg/every day divided bid po; Aza Imuran® 5 mg/kg qod po for two weeks conditioning period. The drugs are then administered at that dose for an additional two weeks in the presence of toleragen. Doses are halved for all drugs each 2 weeks after first toleragen infusion. Patients are monitored for adverse reactions, and for CsA peak and trough levels.

Toleragen. Recombinant α-L-iduronidase is produced in Chinese-hamster-ovary cells with the use of bioreactors and standard column chromatography, and extensively analyzed for safety and purity. The activity of α-L-iduronidase is measured according to the method of Shull et al. supra., or with an assay whose results are reported in SI units (Kakkis et al., 2001, supra). When the latter assay is used, a dose of 125,000 U of α-L-iduronidase per kilogram is equivalent to 100 SI units per kilogram. Urinary glycosaminoglycan excretion is measured according to an adaptation of the method of Bjomsson. Enzyme-linked immunosorbent assays for antibodies to α-L-iduronidase uses a variation of the method of Shull et al., and Western blotting is performed according to a standard method.

The toleragen is administered by intravenous infusion (diluted in normal saline with 0.1 percent human serum albumin) at a dose of 14,000 U (0.056 mg)/kg, delivered weekly. The first dose is given after completion of the two week conditioning period, and weekly thereafter. Patients are premedicated with diphenhydramine (0.5 to 1.25 mg per kilogram of body weight).

After induction of tolerance, usually 6 to 8 weeks after initiation of the conditioning period, the dose is increased to once weekly, 125,000 U (0.58 mg) per kilogram; the rate is 3000 Upper kilogram during the first hour and 61,000 Upper kilogram during each of the following two hours.

Example 7

Immune Tolerance Regimen Prevents the Induction of Other Immunoglobulins in Addition to IgG The tolerance regimen in canine prevents the induction of IgG as manifested by a decrease in total IgG response against iduronidase as compared to the IgG response observed in non-tolerant canines. The present Example provides additional evidence that shows that in addition to preventing the induction of IgG, the tolerizing regimen prevents the induction of other immunoglobulins subtypes also. Analyses of the immune sera of canines that were either tolerant (dogs PE and SA) or canine controls (dogs RU and UM) that had not received the tolerizing regimen were studied for the presence of IgG, IgA and IgE antibodies to iduronidase.

The data from these determinations are shown in FIGS. 7A to 7D. These data show that tolerant dogs did not have a significant increase (>3 fold) in titer in these other subtypes and non-tolerant dogs did have a significant IgA or IgE response ~10 fold in some cases. Although the IgA and IgE titers were not high relative to IgG, these titers were significant and positive in the non-tolerant canines. The data show that the tolerance regimen also prevents other Ig subtypes from being induced consistent with a broader effect on the humoral response.

Example 8

Induction of Tolerance in Animals with Pre-Existing Immune Response

In another aspect of the present invention, the inventors demonstrated that it is possible to reduce or eliminate an existing immune response. The present Example discusses data generated from the canine Nitro. Nitro was originally tolerized, but after a period of nearly 6 months of hiatus from antigen exposure, a reexposure induced a profound anamnestic response with a titer reaching 400+. After several weeks without exposure to antigen, the canine was placed on the tolerance regimen and given low dose (0.056 mg) weekly infusions of iduronidase. The titer initially rose during the administration of the CsA+Aza regimen to greater than 100 in a typical anamnestic response and than rapidly fell to below 20 (see FIG. 8). The response was reduced by the regimen and the immune response to enzyme is relatively muted compared with the >400 level previously on 0.5 mg/kg/wk infusions. These data demonstrate that it is possible to reinduce the tolerance to the toleragen even if the animal already possesses an immune response against the antigen in the toleragen composition.

Example 9

Presence of High Affinity Uptake Residue on the Antigen Renders Antigen More Effective as a Toleragen The effects of a high affinity moiety on the toleragen were discussed in Example 1 above, which showed that the use of a moiety such as mannose-6-phosphate may be useful in augmenting the tolerizing capability in an antigen. This aspect of the toleragen compositions was investigated further and the results are reported in the present Example and in FIG. 9. Iduronidase normally comprises a mannose-6-phoshate and this high uptake moiety facilitates the uptake of the iduronidase by the target cells via a mannose-6 phosphate receptor.

In the present example, recombinant iduronidase was dephosphorylated by incubation with acid phosphatase bound to beads. The enzyme was successfully dephosphorylated as demonstrated by the lack of efficient uptake in Hurler fibroblasts and a $K_{uptake}$ that was too low to be calculated. The dephospho-idurondase was used in a tolerization regimen similar to the tolerization experiments conducted with the iduronidase discussed in the above examples. The data are shown in FIG. 9. This study showed that the canine tolerized with dephospho-iduronidase was not able to tolerize, again suggesting that high uptake affinity is needed for tolerance.

Example 10

Methods of Inducing Tolerance to Factor VIII

Treatment of hemophilia A relies on the ability to deliver an effective amount of Factor VIII to the hemophiliac. However, antibodies or inhibitors to Factor VIII therapy can be a significant problem in patients with hemophilia A disease. Hemophiliac patient that have developed antibody inhibitors to Factor VIII may experience uncontrolled bleeding rendering the FactorVIII therapy ineffective. Examples 1-9 describe methods and compositions for inducing an antigen specific immune tolerance administration of α-L-iduronidase or alpha-glucosidase as a toleragen in combination with a regimen of immunosuppression for a period of time sufficient to tolerize the host to the toleragen. The present example is directed to inducing immune tolerance to Factor VIII. The present example provides a protocol to be used to prevent and reverse the formation of inhibitor against Factor VIII.

Preparation of a Toleragenic Factor VIII: the Toleragenic Factor VIII is made by conjugating the protein to a high uptake protein. In the simplest approach Factor VIII protein is conjugated using a lysosomal enzyme, iduronidase that contains a high affinity uptake marker on its N-linked carbohydrates. The proteins are conjugated using a heterobifunctional cross-linking agent (SBDB for example). Optimally, the cross-linking would occur at a ratio of 1:1 and the cross-linked proteins purified.

Tolerization of a hemophilia patients: The patient would receive cyclosporin A at a dose expected to be 12.5 mg/kg/d divided to achieve a blood level of greater than 400 ng/ml. The patient would also receive Azathioprine at 2-5 mg/kg every other day as appropriate for a human patient. After 18 days of the drugs, the patient would receive 0.6 mg/kg of toleragen in an infusion on a weekly basis. After day 32, the CsA and Aza are cut in half in dose size and after day 46 the drugs are cut to ¼. On day 60, the CsA+Aza is terminated and the weekly infusions continued. Monitoring of the immune response would show only a modest if any response that was less than 20% fold the prior response without tolerance. The patient receives normal factor VIII infusions and the toleragen is terminated. If needed, additional toleragen may be administered to maintain the tolerant state at intervals.

Example 11

Tolerance to β-Cell Antigens in Diabetes

Antibodies and cellular immune responses to β-cell antigens, such as, glutamic acid decarboxylase (GAD) are responsible for the destruction of the pancreatic β-cell and the onset of diabetes. The induction of tolerance to these antigens would provide an important method to prevent the progression and onset of diabetes in patients at risk or having onset of Type 1 diabetes symptoms. GAD is one important antigen but other antigens such as IA2 and insulin could also be studied this way.

Preparation of a Toleragenic GAD. The Toleragenic from of GAD may be made by fusion with a high-uptake peptide moiety. The gene for human GAD is connected in frame with the gene for a high uptake peptide such as IGF2, that is known to bind the mannose 6-phosphate receptor. Such a fusion would allow both proteins to be made in the right structure and with the right antigenicity and form.

Tolerization of a type 1 diabetes patients. A new onset diabetes patient who was early in the course of the disease and retained some β-cell function, would preferably be used. The patient would receive cyclosporin A at a dose expected to be 12.5 mg/kg/d divided bid to achieve a blood level of greater than 400 ng/ml. The patient would also receive azathioprine at 2-5 mg/kg every other day as appropriate for a human patient. After 18 days of the drugs, the patient would receive 0.06 mg/kg of toleragen in an infusion on a weekly basis. After day 32, the CsA and Aza may be cut in half in dose size and after day 46 the drugs may be cut to ¼. On day 60, the CsA+Aza is terminated and the weekly infusions continued. The toleragen dose may be then increased to 0.6 mg/kg each week. Monitoring of the immune response would likely show only a modest if any response that was less than 20% fold the prior response without tolerance. The patient would have normalized glucose tolerance and the toleragen would be terminated. If needed, additional toleragen could be administered to maintain the tolerant state at intervals to be determined by the clinical condition of the patient.

What is claimed is:

1. A method of decreasing an antibody response to an administered soluble therapeutic polypeptide in a mammalian host, comprising the steps of:
   (a) administering to the mammalian host for at least about two weeks effective amounts of (i) cyclosporine A and (ii) azathioprine, wherein the cyclosporine A is maintained at a trough blood level of at least 200 ng/ml, and wherein the azathioprine is administered at a dose of at least 2.5 mg/kg/day;
   (b) after step (a), administering to the mammalian host for at least about two weeks effective amounts of (i) cyclosporine A, (ii) azathioprine, and (iii) a soluble form of the therapeutic polypeptide that naturally comprises or is conjugated to a mannose-6-phosphate high uptake moiety, wherein the cyclosporine A is maintained at a trough blood level of at least 200 ng/ml, and wherein the azathioprine is administered at a dose of at least 2.5 mg/kg/day;
   (c) after step (b), discontinuing administration of cyclosporine A and azathioprine; and
   (d) after step (c), administering the soluble therapeutic polypeptide,
   wherein during step (d) the mammalian host exhibits an antibody titer to the soluble therapeutic polypeptide in the absence of continued immune suppression that is decreased compared to the antibody titer induced by the soluble therapeutic polypeptide in a mammalian host that has not undergone steps (a)-(c).

2. The method according to claim 1, wherein a trough level of cyclosporine A during said administering step (a) is about 200 ng/ml to about 500 ng/ml, and said trough level is sufficient to suppress host T cell responses.

3. The method according to claim 2, wherein a trough level of cyclosporine A during step (a) is at least about 300 ng/ml.

4. The method according to claim 2, wherein a trough level of cyclosporine A during step (a) is at least about 400 ng/ml.

5. The method according to claim 1, wherein during step (b) the administration of cyclosporine A and azathioprine is continued for a period of at least about 6 weeks.

6. The method according to claim 1, wherein said azathioprine is administered every other day at a dose of 5 mg/kg/day.

7. The method according to claim 1, comprising: administering during step (b) an effective dose of the soluble therapeutic polypeptide at least 6 times during a period of at least about 6 weeks.

8. The method according to claim 1, wherein during step (b) the administration of cyclosporine A and azathioprine is continued for a period of at least about 3 weeks.

9. The method according to claim 1, comprising: administering during step (b) an effective dose of said the soluble therapeutic polypeptide at least 3 times during a period of at least about 3 weeks.

10. The method according to claim 1, wherein the azathioprine in step (a) is administered at a dose of 2.5 mg/kg/day.

11. The method according to claim 1, wherein after step (b), the cyclosporine A and azathioprine are tapered by administering reduced amounts of cyclosporine A and azathioprine.

12. The method according to claim 1, wherein during step (b) the dose of soluble therapeutic polypeptide is 50% or less than of the therapeutic dose of the soluble therapeutic polypeptide.

13. The method according to claim 1, wherein during step (b) the dose of soluble therapeutic polypeptide is 10% or less than the therapeutic dose of the soluble therapeutic polypeptide.

14. The method according to claim 1, wherein the therapeutic polypeptide is a polypeptide for which a high uptake receptor is widely expressed in said mammalian host.

15. The method according to claim 1, wherein in step (b) the soluble therapeutic polypeptide is conjugated to a moiety comprising mannose-6-phosphate.

16. The method according to claim 1, wherein the therapeutic polypeptide comprises mannose-6-phosphate.

17. The method according to claim 1, wherein the therapeutic polypeptide is selected from the group consisting of antibodies, clotting factors, enzymes, and growth factors.

18. The method according to claim 1, wherein the therapeutic polypeptide is an autoantigen.

19. The method according to claim 18, wherein the therapeutic polypeptide comprises a plurality of autoantigens.

20. The method according to claim 1, wherein the therapeutic polypeptide comprises a transplantation antigen.

21. The method according to claim 20, wherein the therapeutic polypeptide comprises a plurality of transplantation antigens.

22. The method according to claim 17, wherein the clotting factor is Factor VIII.

23. The method according to claim 22, wherein the Factor VIII is conjugated to a high uptake moiety.

24. The method according to claim 23, wherein the high uptake moiety is iduronidase comprising a high affinity uptake marker on its N-linked carbohydrates.

25. The method according to claim 1, wherein the therapeutic polypeptide comprises a β-cell antigen.

26. The method according to claim 25, wherein the β-cell antigen is selected from the group consisting of glutamic acid decarboxylase (GAD), IA2 and insulin.

27. The method according to claim 26, wherein said β-cell antigen is GAD.

28. The method according to claim 27, wherein the GAD is conjugated to a high uptake moiety.

29. The method according to claim 28, wherein the high uptake moiety is a peptide that binds to a receptor selected from the group consisting of transferrin receptor, melanotransferrin receptor and mannose-6-phosphate receptor.

30. The method according to claim 29, wherein the high uptake moiety is a peptide that binds to a mannose-6-phosphate receptor.

31. The method according to claim 30, wherein said peptide is insulin-like growth factor-2 (IGF2).

32. The method according to claim 1, wherein the mammalian host was previously exposed to said therapeutic polypeptide prior to step (a).

33. A method of decreasing an antibody response to an administered soluble therapeutic polypeptide in a mammalian host, comprising the steps of:
  (a) administering to the mammalian host for at least about two weeks effective amounts of (i) cyclosporine A and (ii) an anti-proliferative agent selected from the group consisting of a nucleotide analog and an anti-metabolite drug, wherein the cyclosporine A is maintained at a trough blood level of at least 200 ng/ml and wherein the anti-proliferative agent is administered at a dose effective to decrease the antibody titer to the soluble therapeutic polypeptide during step (d);
  (b) administering to the mammalian host for at least about two weeks effective amounts of (i) cyclosporine A, (ii) an anti-proliferative agent selected from the group consisting of a nucleotide analog and an anti-metabolite drug and (iii) a soluble form of a therapeutic polypeptide that naturally comprises or is conjugated to a mannose-6-phosphate high uptake moiety, wherein the cyclosporine A is maintained at a trough blood level of at least 200 ng/ml and wherein the anti-proliferative agent is administered at a dose effective to decrease the antibody titer to the soluble therapeutic polypeptide during step (d);
  (c) after step (b), discontinuing administration of cyclosporine A and the anti-proliferative agent; and
  (d) after step (c), administering the soluble therapeutic polypeptide, wherein during step (d) the mammalian host exhibits an antibody titer to the soluble therapeutic polypeptide in the absence of continued immune suppression that is decreased compared to the antibody titer induced by the soluble therapeutic polypeptide in a mammalian host that has not undergone steps (a)-(c).

34. The method according to claim 33, wherein the nucleotide analog is a 6-mercaptopurine drug.

35. The method according to claim 34, wherein the 6-mercaptopurine drug is azathioprine.

36. The method according to claim 33, wherein the anti-metabolite drug is an inhibitor of dihydrofolate reductase or a nucleotide metabolism enzyme.

37. The method according to claim 36, wherein the inhibitor is methotrexate or an analog thereof.

* * * * *